(12) United States Patent
Mou et al.

(10) Patent No.: US 10,908,137 B2
(45) Date of Patent: *Feb. 2, 2021

(54) ACTUATING AND SENSING MODULE

(71) Applicant: Microjet Technology Co., Ltd., Hsinchu (TW)

(72) Inventors: Hao-Jan Mou, Hsinchu (TW); Ching-Sung Lin, Hsinchu (TW); Chi-Feng Huang, Hsinchu (TW); Yung-Lung Han, Hsinchu (TW); Hsuan-Kai Chen, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 153 days.

This patent is subject to a terminal disclaimer.

(21) Appl. No.: 16/277,609

(22) Filed: Feb. 15, 2019

(65) Prior Publication Data

US 2019/0302076 A1    Oct. 3, 2019

(30) Foreign Application Priority Data

Mar. 30, 2018  (TW) .............................. 107111394 A

(51) Int. Cl.
*G01N 33/00* (2006.01)
*F04B 37/18* (2006.01)
(Continued)

(52) U.S. Cl.
CPC ......... *G01N 33/0047* (2013.01); *F04B 37/18* (2013.01); *F04B 43/043* (2013.01);
(Continued)

(58) Field of Classification Search
CPC .......... F04B 37/18; G08B 17/10; G01N 33/00
See application file for complete search history.

(56) References Cited

U.S. PATENT DOCUMENTS 9,875,631 B2 * 1/2018 Mittleman ............ G08B 17/00
2010/0229658 A1  9/2010 Glezer et al.
(Continued)

FOREIGN PATENT DOCUMENTS

CN    1157601 C     7/2004
EP    2733484 A1    5/2014
(Continued)

OTHER PUBLICATIONS

Extended European Search Report, dated Sep. 20, 2019, for European Application No. 19157161.1.

*Primary Examiner* — Jamel E Williams
(74) *Attorney, Agent, or Firm* — Birch, Stewart, Kolasch & Birch, LLP

(57) ABSTRACT

An actuating and sensing module is provided. The actuating and sensing module includes a main body, a particle monitoring base, a plurality of actuators and a plurality of sensors. The main body includes a first separating chamber having a first compartment and a second compartment and a second separating chamber having a third compartment and a fourth compartment. The plurality of actuators include a first actuator disposed between the second compartment and the first partition and a second actuator disposed within the accommodation recess. The plurality of sensors include a first sensor, a second sensor and a third sensor. The first sensor is disposed in the first compartment for monitoring the gas. The second sensor is disposed in the third compartment for monitoring the gas in the third compartment. The third sensor is located in the monitoring channel for monitoring the gas in the monitoring channel.

10 Claims, 20 Drawing Sheets

(51) Int. Cl.
    *F04B 43/04*         (2006.01)
    *F04B 45/047*      (2006.01)

(52) U.S. Cl.
    CPC .......... *F04B 43/046* (2013.01); *F04B 45/047* (2013.01); *G01N 33/004* (2013.01); *G01N 33/0009* (2013.01); *G01N 33/0016* (2013.01); *G01N 33/0031* (2013.01); *G01N 33/0039* (2013.01)

(56) References Cited

U.S. PATENT DOCUMENTS

2014/0377099 A1    12/2014    Hsueh et al.
2015/0338390 A1    11/2015    Anglin, Jr. et al.
2019/0302075 A1*  10/2019    Mou ..................... F04B 43/046

FOREIGN PATENT DOCUMENTS

JP              5692465 B2    4/2015
TW            M553862 U    1/2018
WO    WO 2018/006932 A1    1/2018

\* cited by examiner

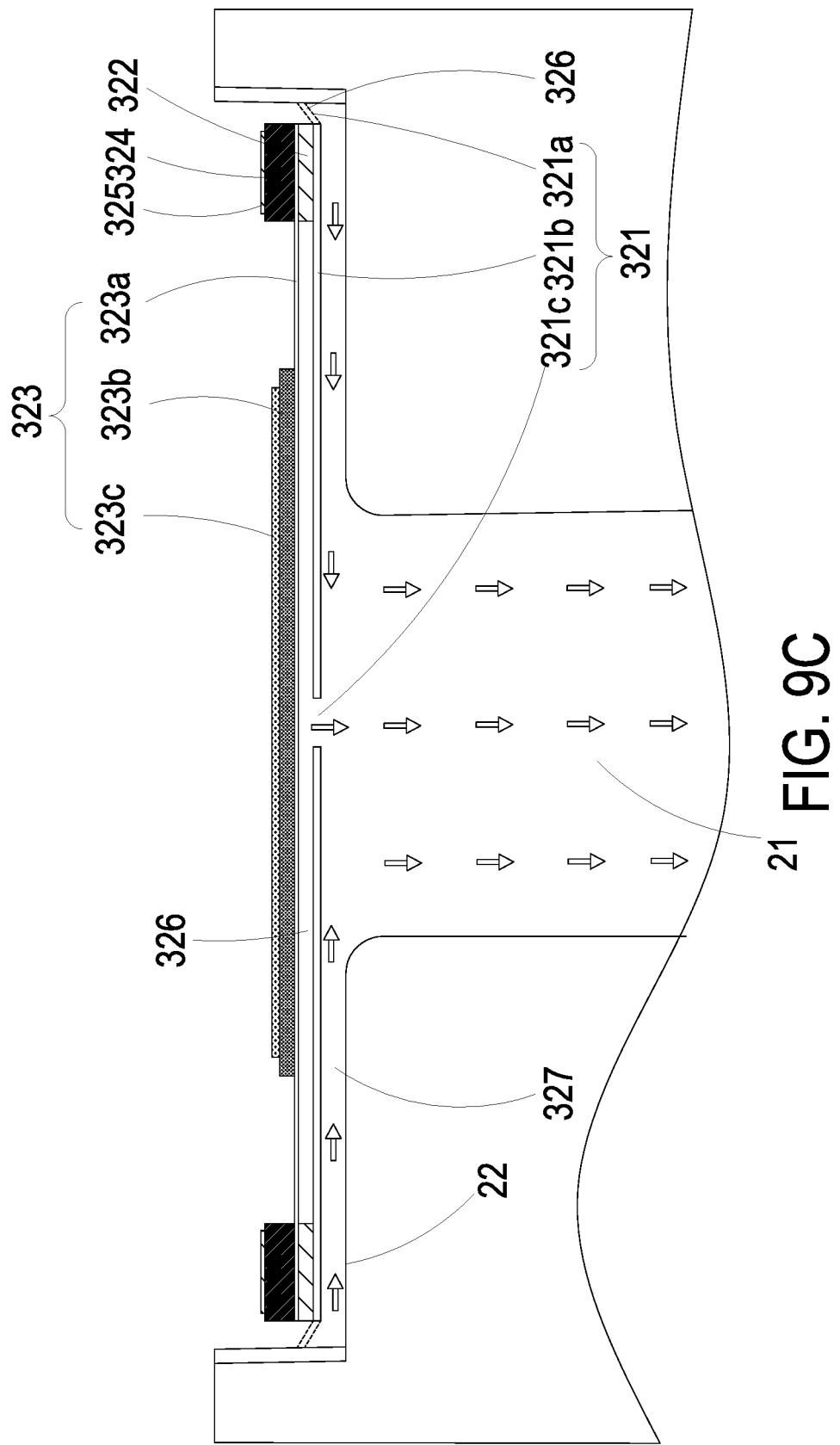

ACTUATING AND SENSING MODULE

FIELD OF THE INVENTION

The present disclosure relates to an actuating and sensing module, and more particularly to an actuating and sensing module assembled in a thin portable device for monitoring gas.

BACKGROUND OF THE INVENTION

Nowadays, people pay much attention to the air quality in the environment. For example, it is important to monitor carbon monoxide, carbon dioxide, volatile organic compounds (VOC), Particulate Matter 2.5 (PM2.5), nitric oxide, sulfur monoxide, and so on. The exposure of these substances in the environment will cause human health problems or even threaten the human life. Therefore, it is important for every country to improve the air quality.

Generally, it is feasible to use a gas sensor to monitor the air quality in the environment. If the gas sensor is capable of immediately providing people with the monitored information relating to the environment for caution, it may help people escape or prevent from the injuries and influence on human health caused by the exposure of the substances described above in the environment. In other words, the gas sensor is suitably used for monitoring the ambient gas in the environment.

Nowadays, the gas sensor monitors the environmental gas transported to the surface of the gas sensor. If there is no actuator for guiding the gas and increasing the flow rate of the gas, the time of the gas flowing to the gas sensor may be too long, which reduces the efficiency of sensing. However, if the actuator is added to construct an actuating and sensing module, the heat is generated by the high-speed and continuous vibration of the actuator during operation. The generated heat is transferred to the surrounding of the gas sensor constantly. Therefore, the heat makes the gas to be sensed around the gas sensor different from the gas around the actuating and sensing module, and the monitoring result of the gas sensor is affected. In addition, when the actuating and sensing module is applied on and assembled with a device (e.g., portable electronic device), some interfering substances (e.g., gas pollution and heat) may be generated inside the device during the operation of the electronic elements (e.g., circuit board and processor) within the device. When the interfering substances are guided into the actuating and sensing module or mixed with the gas to be sensed, the monitoring quality of the gas sensor is affected. Namely, the actual characteristics and components of the gas to be sensed around the actuating and sensing module cannot be sensed, and the sensing result is inaccurate.

Therefore, there is a need of providing an actuating and sensing module for increasing the efficiency of sensing, monitoring the gas to be sensed certainly, and decreasing the effect of the extrinsic factor on the gas sensor.

SUMMARY OF THE INVENTION

An object of the present disclosure provides an actuating and sensing module capable of being assembled in a thin portable device for monitoring the gas. The actuating and sensing module includes a main body, an actuator and a gas sensor. The disposition of the actuator increases the rate of transporting the gas to the surface of the gas sensor for monitoring, and thus the sensing efficiency of the gas sensor is enhanced. Moreover, the main body has a monitoring chamber with one-way opening for introducing or discharging the gas in single direction. More specifically, the monitoring chamber has two openings, one for inhaling the air and the other one for discharging the air. The air inhaled in the monitoring chamber does not flow back along the same path to be discharged from the same opening. The actuator drives the resonance plate to transport the gas. Therefore, the gas outside the thin portable device is guided thereinto by the actuating and sensing module for monitoring. The characteristic of the gas to be monitored within the actuating and sensing module is the same as the characteristic of the gas outside the thin portable device.

In accordance with an aspect of the present disclosure, an actuating and sensing module is provided. The actuating and sensing module includes a main body, a particle monitoring base, a plurality of actuators and a plurality of sensors. The main body includes a plurality of separating chambers, and the plurality of separating chambers include a first separating chamber and a second separating chamber. The first separating chamber has a first partition, a first inlet and a first outlet. An interior space inside the first separating chamber is divided into a first compartment and a second compartment by the first partition. The first inlet is in fluid communication with the first compartment. The first outlet is in fluid communication with the second compartment. The first partition has a first communicating hole, and the first compartment and the second compartment are in fluid communication with each other through the first communicating hole. The second separating chamber is assembled with the first separating chamber as a whole and has a supporting partition, a second inlet, and a second outlet. An interior space inside the second separating chamber is divided into a third compartment and a fourth compartment by the supporting partition. The second inlet is in fluid communication with the third compartment. The second outlet is in fluid communication with the fourth compartment. The supporting partition has a second communicating hole, and the third compartment and the fourth compartment are in fluid communication with each other through the second communicating hole. The particle monitoring base is disposed between the third compartment and the supporting partition of the second separating chamber. The particle monitoring base has a monitoring channel, and an accommodation recess. The accommodation recess is disposed on an end of the monitoring channel and in fluid communication with the monitoring channel. The plurality of actuators include a first actuator and a second actuator. The first actuator is disposed between the second compartment and the first partition. Gas is introduced into the first compartment through the first inlet, transported to the second compartment through the first communicating hole, and discharged through the first outlet by the first actuator. One-way gas transportation in the first separating chamber is formed. The second actuator is disposed within the accommodation recess of the particle monitoring base and seals the end of the monitoring channel. The gas is introduced into the third compartment through the second inlet, guided into the monitoring channel, transported to the fourth compartment through the second communicating hole, and discharged through the second outlet by the second actuator. One-way gas transportation in the second separating chamber is formed. The plurality of sensors include a first sensor, a second sensor and a third sensor. The first sensor is disposed in the first compartment and is separated from the first actuator. The first sensor is configured to monitor the gas on a surface of the first sensor. The second sensor is disposed in the third compartment and is configured to monitor the gas guided into the third compartment. The third sensor is carried on the supporting partition and is located in the monitoring channel of the particle monitoring base. The third sensor is configured to monitor the gas guided into the monitoring channel.

The above contents of the present disclosure will become more readily apparent to those ordinarily skilled in the art after reviewing the following detailed description and accompanying drawings, in which:

BRIEF DESCRIPTION OF THE DRAWINGS

FIG. 9B and FIG. 9C schematically illustrate the actions of the second actuator of the actuating and sensing module assembled on the particle monitoring base;

DETAILED DESCRIPTION OF THE PREFERRED EMBODIMENT

Figure 1:
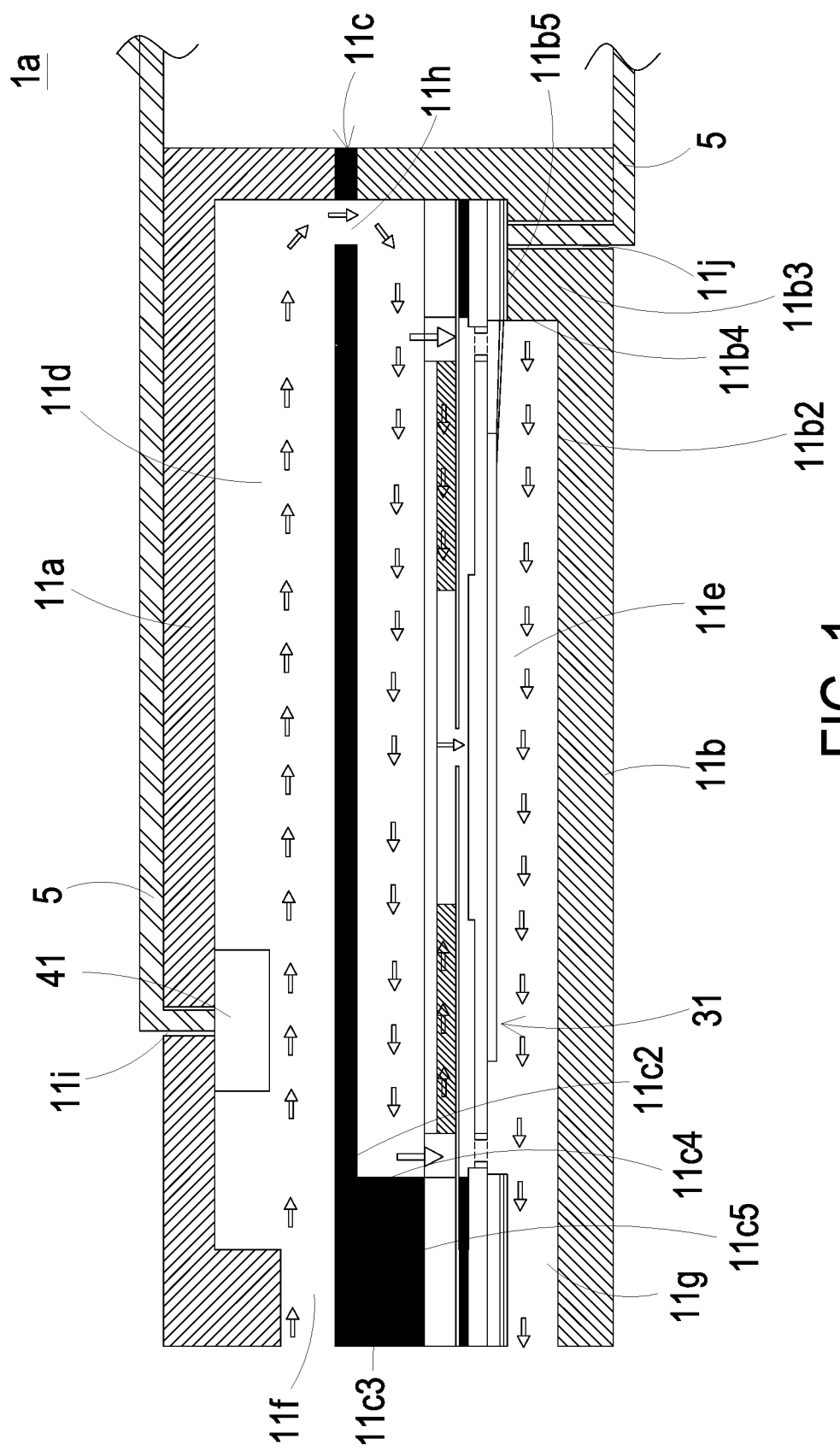
FIG. 1 is a schematic cross-sectional view illustrating a first separating chamber of an actuating and sensing module according to an embodiment of the present disclosure.

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Please refer to FIGS. 1 to 3 and FIGS. 5 to 6B. The present discourse provides an actuating and sensing module including at least one main body 1, at least one particle monitoring base 2, a plurality of actuators, a plurality of sensors, at least one first separating chamber 1a, at least one second separating chamber 1b, at least one first partition 11c, at least one first compartment 11d, at least one second compartment 11e, at least one first inlet 11f, at least one first outlet 11g, at least one first communicating hole 11h, at least one supporting partition 12c, at least one third compartment 12d, at least one fourth compartment 12e, at least one second inlet 12f, at least one second outlet 12g, at least one second communicating hole 12h, at least one monitoring channel 21, at least one accommodation recess 22, at least one first actuator 31, at least one second actuator 32, at least one first sensor 41, at least one second sensor 42 and at least one third sensor 43. The number of the main body 1, the particle monitoring base 2, the first separating chamber 1a, the second separating chamber 1b, the first partition 11c, the first compartment 11d, the second compartment 11e, the first inlet 11f, the first outlet 11g, the first communicating hole 11h, the supporting partition 12c, the third compartment 12d, the fourth compartment 12e, the second inlet 12f, the second outlet 12g, the second communicating hole 12h, the monitoring channel 21, the accommodation recess 22, the first actuator 31, the second actuator 32, the first sensor 41, the second sensor 42 and the third sensor 43 is exemplified by one for each in the following embodiments but not limited thereto. It is noted that each of the main body 1, the particle monitoring base 2, the first separating chamber 1a, the second separating chamber 1b, the first partition 11c, the first compartment 11d, the second compartment 11e, the first inlet 11f, the first outlet 11g, the first communicating hole 11h, the supporting partition 12c, the third compartment 12d, the fourth compartment 12e, the second inlet 12f, the second outlet 12g, the second communicating hole 12h, the monitoring channel 21, the accommodation recess 22, the first actuator 31, the second actuator 32, the first sensor 41, the second sensor 42 and the third sensor 43 can also be provided in plural numbers.

The present disclosure provides an actuating and sensing module. Please refer to FIGS. 1 to 5. The actuating and sensing module includes a main body 1, a particle monitoring base 2, a plurality of actuators and a plurality of sensors. Please refer to FIGS. 3 to 5. The main body 1 includes a plurality of separating chambers assembled together. The plurality of separating chambers include a first separating chamber 1a and a second separating chamber 1b assembled together as a whole. The plurality of actuators include a first actuator 31 and a second actuator 32. The plurality of sensors include a first sensor 41, a second sensor 42 and a third sensor 43.

As shown in FIG. 1, the first separating chamber 1a includes a first body 11a, a second body 11b and a first partition 11c, and the first body 11a and the second body 11b are assembled with each other. The first partition 11c is disposed between the first body 11a and the second body 11b. Thus, the first partition 11c defines a first compartment 11d and a second compartment 11e within the interior space enclosed by the first body 11a and the second body 11b. There is a first inlet 11f between the first body 11a and the first partition 11c, and the first inlet 11f is in fluid communication with the first compartment 11d. There is a first outlet 11g between the second body 11b and the first partition 11c, and the first outlet 11g is in fluid communication with the second compartment 11e. Both of the first inlet 11f and the first outlet 11g are disposed on the same side of the first separating chamber 1a. In addition, the first partition 11c has a first communicating hole 11h, and the first compartment 11d and the second compartment 11e are in fluid communication with each other through the first communicating hole 11h. The first inlet 11f, the first compartment 11d, the first communicating hole 11h, the second compartment 11e and the first outlet 11g forms a one-way gas channel within the main body 1 for transporting and discharging the gas (the path illustrated by the arrows in FIG. 1). Rather than being inhaled and discharged by the same opening, the gas is inhaled from the first inlet 11f, flows along the one-way gas channel, and then is discharged through the first outlet 11g into the environment outside the first separating chamber 1a. The first actuator 31 is sealed and disposed between the second body 11b and the first partition 11c. In this embodiment, the first actuator 31 is located between the second compartment 11e and the first partition 11c. One end of the first actuator 31 is securely mounted on the second body 11b, the other end of the first actuator 31 is securely mounted on the first partition 11c, and thus the second compartment 11e is sealed, which will be described in more detail below. The first partition 11c has an inner surface 11c2 and a protrusion portion 11c3 protruding from the inner surface 11c2. The protrusion portion 11c3 has a top surface 11c5 and a sidewall 11c4 extending from the inner surface 11c2 to connect to the top surface 11c5. The second body 11b has an inner surface 11b2 and a protrusion portion 11b3 protruding from the inner surface 11b2. The protrusion portion 11b3 has a top surface 11b5 and a sidewall 11b4 extending from the inner surface 11b2 to connect to the top surface 11b5. One end of the first actuator 31 attaches to the top surface 11c5, and seals the edge of the sidewall 11c4 of the protrusion portion 11c3. The other end of the first actuator 31 attaches to the top surface 11b5, and seals the edge of the sidewall 11b4 of the protrusion portion 11b3. In other words, the protrusion portion 11c3 and the protrusion portion 11b3 extends in opposite directions toward each other, thereby providing two platforms for supporting the first actuator 31. Also, the design of the protrusion portion 11c3 allows one part of the gas channel to be formed between the first actuator 31 and the first partition 11c, and the design of the protrusion portion 11b3 allows another part of the gas channel to be formed between the first actuator 31 and the second body 11b. The first actuator 31 is actuated to transport the gas, so that a negative pressure is formed in the first compartment 11d. The negative pressure allows the gas to be inhaled through the first inlet 11f to the first compartment 11d, and the gas flows to the second compartment 11e through the first communicating hole 11h. As the first actuator 31 is continuously actuated to transport the gas, the gas in the second compartment 11e is pushed and discharged from the first outlet 11g into the environment outside the first separating chamber 1a. Consequently, the one-way gas transportation is realized. The first sensor 41 is disposed in the first compartment 11d and is separated from the first actuator 31. The first sensor 41 is configured to monitor the gas flowing on a surface thereof. The first sensor 41 and the first actuator 31 are separated from each other by the first partition 11c. As the first actuator 31 is actuated to transport the gas, the heat is generated due to the continuous vibration of the first actuator 31 at high speed during operation. Under this circumstance, the first partition 11c may function as a barrier, and suppress the interference caused by the generated heat. The first partition 11c prevents the generated heat from interfering with the first sensor 41.

In this embodiment, the first sensor 41 may be a gas sensor including at least one selected from the group consisting of an oxygen sensor, a carbon monoxide sensor, a carbon dioxide sensor, a temperature sensor, an ozone sensor, a volatile organic compound (VOC) sensor and combinations thereof. Alternatively, the first sensor 41 may be a gas detector including at least one selected from a group consisting of a bacterial sensor, a virus sensor, a microorganism sensor and combinations thereof.

Please refer to FIG. 1. The first body 11a of the first separating chamber 1a has a first connecting perforation 11i. The first connecting perforation 11i is configured for the flexible circuit board 5 to penetrate therethrough and connect to the first sensor 41. After connecting the flexible circuit board 5 to the first sensor 41, the first connecting perforation 11i is sealed by a potting compound to prevent the gas from flowing into the first compartment 11d therethrough. The second body 11b of the first separating chamber 1a has a second connecting perforation 11j. The second connecting perforation 11j is configured for the flexible circuit board 5 to penetrate therethrough and connect to the first actuator 31. After connecting the flexible circuit board 5 to the first actuator 31, the second connecting perforation 11j is sealed by the potting compound to prevent the gas from flowing into the second compartment 11e therethrough. Consequently, the actuating and sensing module acts as a monitoring chamber with one-way opening, and the one-way gas transportation and the gas monitoring are realized.

Figure 2:
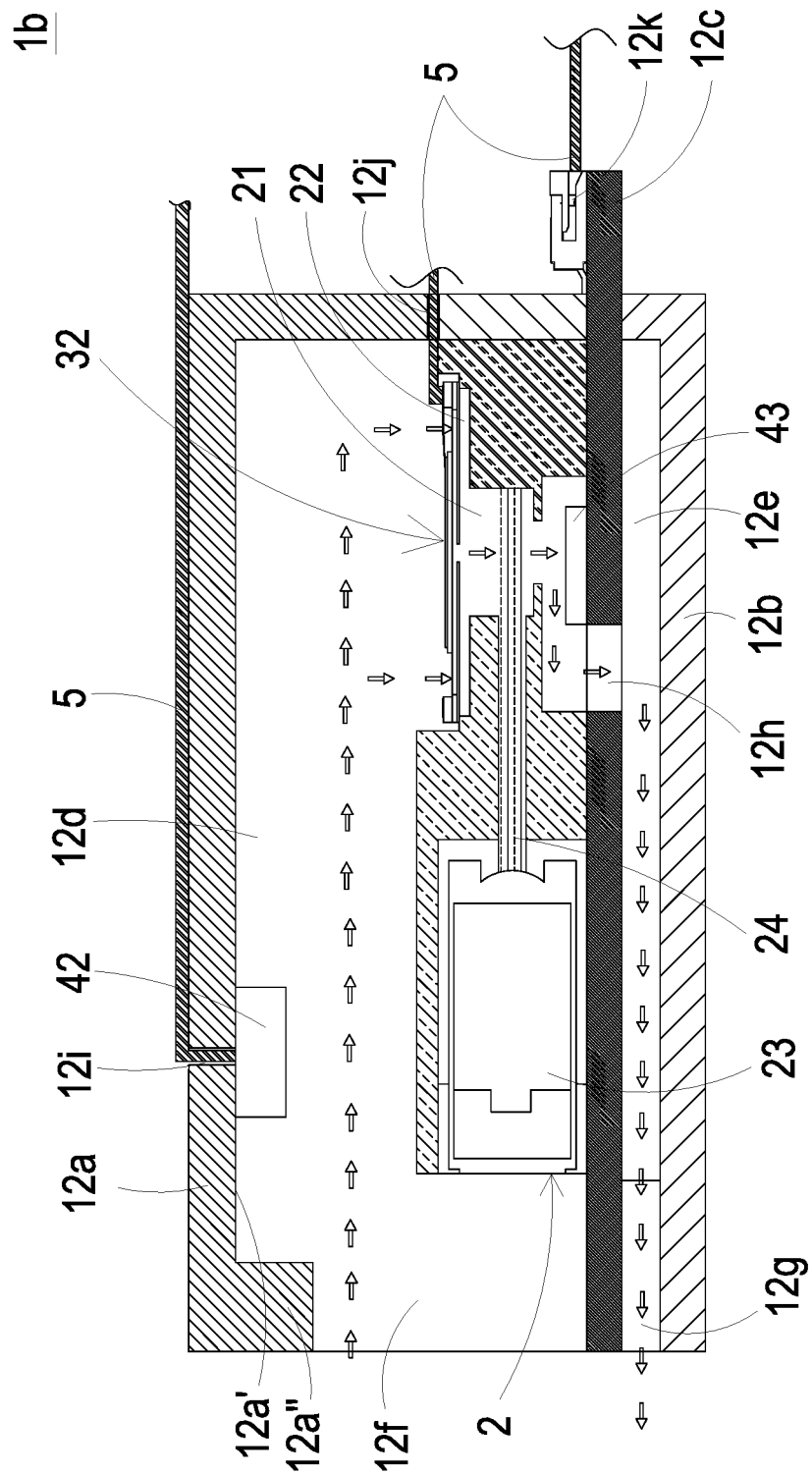
FIG. 2 is a schematic cross-sectional view illustrating a second separating chamber of the actuating and sensing module according to the embodiment of the present disclosure.

Please refer to FIG. 2. The second separating chamber 1b includes a third body 12a, a fourth body 12b and a supporting partition 12c. The third body 12a and the fourth body 12b are assembled with each other. The supporting partition 12c is disposed between the third body 12a and the fourth body 12b. Accordingly, a third compartment 12d is formed between the third body 12a and the supporting partition 12c, and a fourth compartment 12e is formed between the fourth body 12b and the supporting partition 12c. There is a second inlet 12f between the third body 12a and the supporting partition 12c, and the second inlet 12f is in fluid communication with the third compartment 12d. There is a second outlet 12g between the fourth body 12b and the supporting partition 12c, and the second outlet 12g is in fluid communication with the fourth compartment 12e. The third body 12a has an inner surface 12a' and a side portion 12a" protruding from the inner surface 12a'. The side portion 12a" extends toward the fourth body 12b but does not contact the supporting partition 12c. The second sensor 42 is disposed in the third compartment 12d and is configured to monitor the gas within the third compartment 12d. In addition, the supporting partition 12c has a second communicating hole 12h, and the third compartment 12d and the fourth compartment 12e are in fluid communication with each other through the second communicating hole 12h.

The third body 12a has a third connecting perforation 12i and a fourth connecting perforation 12j. The third connecting perforation 12i is configured for the flexible circuit board 5 to penetrate therethrough and connect to the second sensor 42. The fourth connecting perforation 12j is configured for the flexible circuit board 5 to penetrate therethrough and connect to the second actuator 32. After connecting the flexible circuit board 5 to the second sensor 42 and the second actuator 32 respectively, the third connecting perforation 12i and the fourth connecting perforation 12j are sealed by the potting compound to prevent the gas from flowing into the third compartment 12d therethrough. Therefore, the gas is only allowed to flow into the third compartment 12d through the second inlet 12f. The supporting partition 12c has an exposing part (not designated by a reference sign) penetrated and extended to the exterior of the second separating chamber 1b, and a connector 12k is disposed on the exposing part. The connector 12k is configured for inserting flexible circuit board 5 thereinto, and thus the supporting partition 12c is provided with electrical connection and signal connection.

The particle monitoring base 2 is disposed on the supporting partition 12c and is located between the third compartment 12d and the supporting partition 12c of the second separating chamber 1b. The particle monitoring base 2 has a monitoring channel 21. An accommodation recess 22A is disposed on an end of the monitoring channel 21, and the accommodation recess 22 is in fluid communication with the monitoring channel 21. The third sensor 43 is disposed on and supported by the supporting partition 12c, and the third sensor 43 is located in the monitoring channel 21 of the particle monitoring base 2 for sensing the gas within the monitoring channel 21. Preferably but not exclusively, the supporting partition 12c is a circuit board. Therefore, the particle monitoring base 2 and the third sensor 43 disposed on the supporting partition 12c are provided with electrical connection and signal connection via the supporting partition 12c.

In an embodiment, the particle monitoring base 2 further includes a laser device 23 and a beam channel 24. The laser device 23 is electrically connected to the supporting partition 12c. The beam channel 24 extends from the laser device 23 and connects to the monitoring channel 21 perpendicularly. In other words, the beam channel 24 and the monitoring channel 21 are in communication with each other perpendicularly. The beam transmitted by the laser device 23 irradiates the monitoring channel 21 through the beam channel 24. Accordingly, the beam irradiating on the suspension particles in the monitoring channel 21 generates the scattered light points projected on the third sensor 43, and the third sensor 43 monitors the gas via the scattered light points.

Preferably but not exclusively, the third sensor 43 is a light sensor. The light sensor receives the scattered light points generated by the beam irradiating on the suspension particles, and the light sensor calculates the particle diameter and concentration of the suspension particles. In this embodiment, the light sensor is a PM 2.5 (particulate matter 2.5) sensor.

Figure 3:
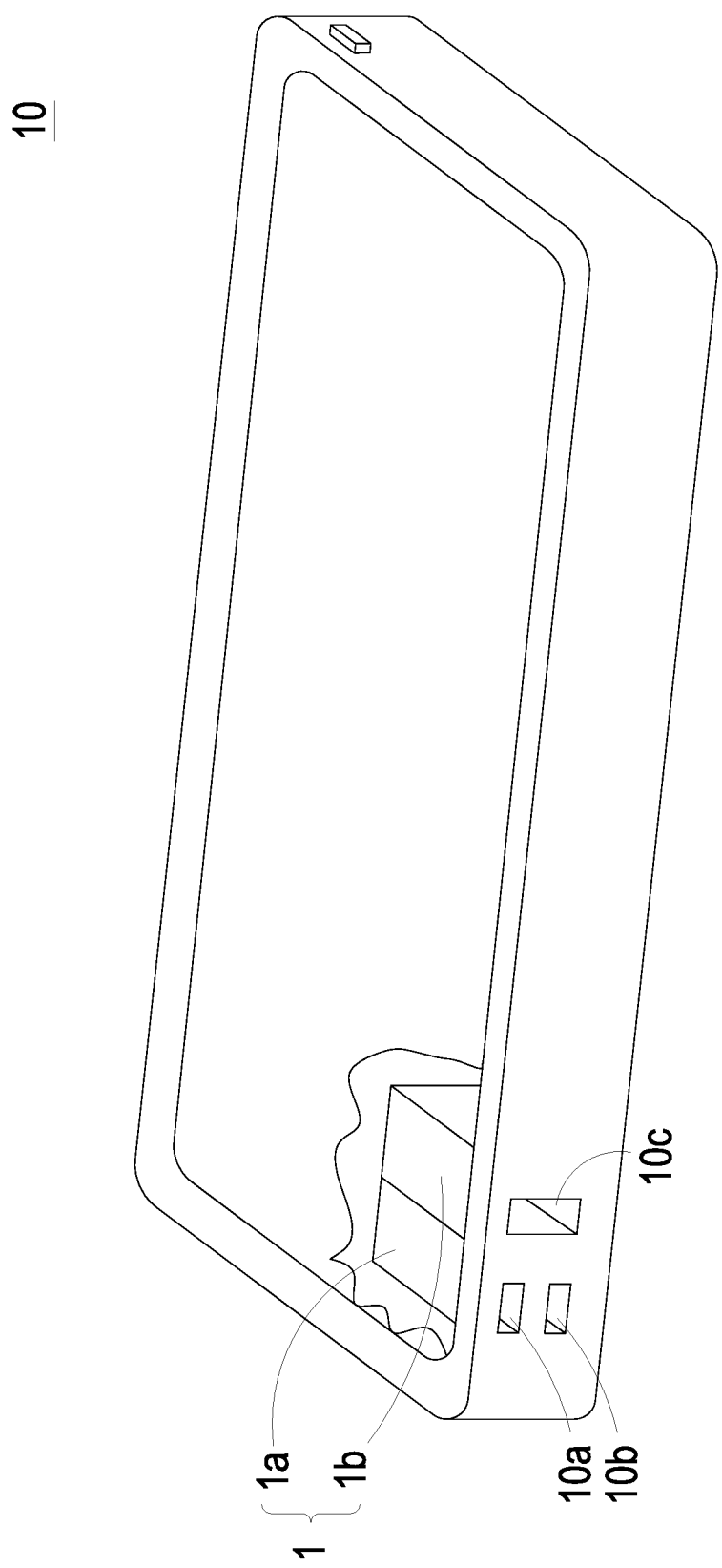
FIG. 3 is a schematic view showing the actuating and sensing module applied in a thin portable device.
Figure 4:
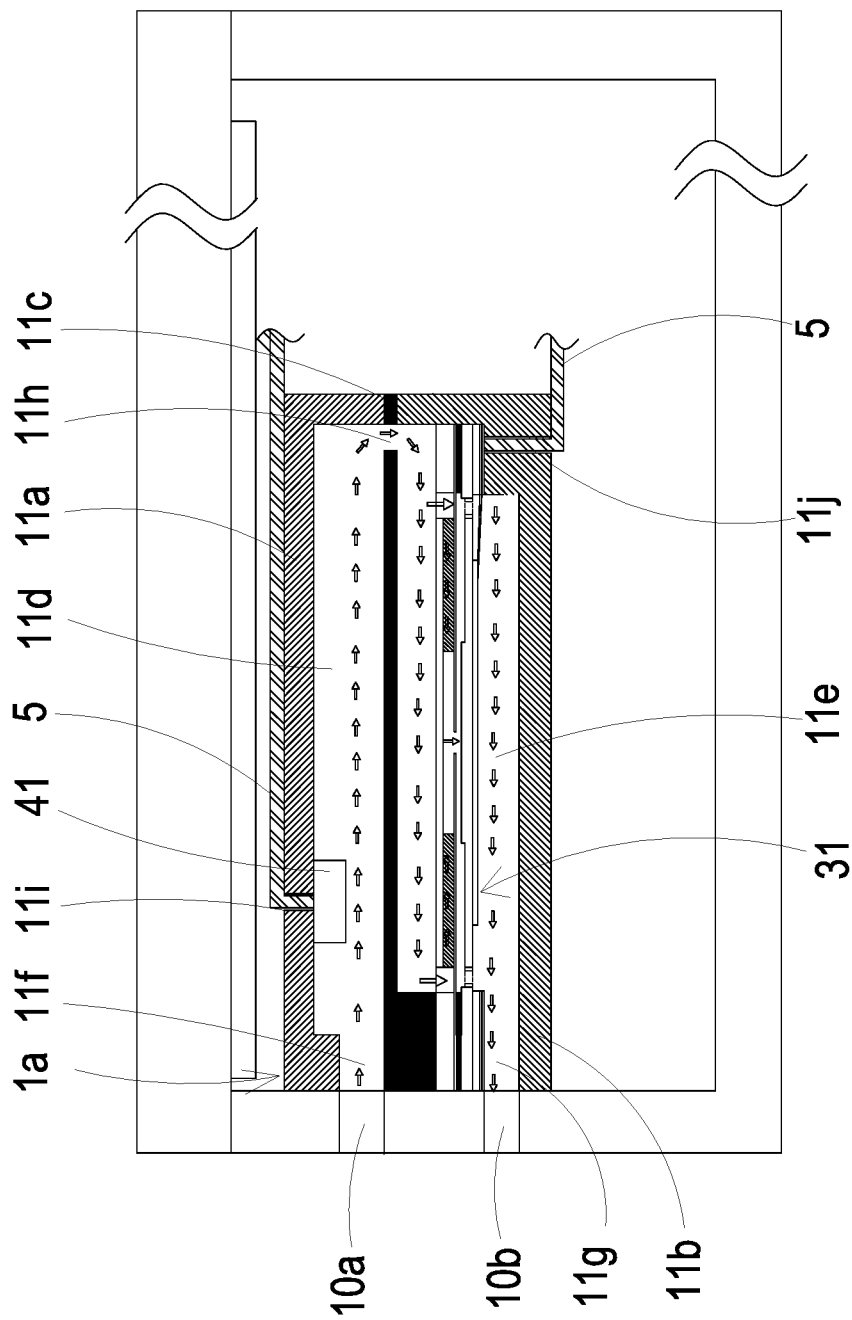
FIG. 4 is a schematic cross-sectional view illustrating the first separating chamber of the actuating and sensing module applied in the thin portable device of FIG. 3.
Figure 5:
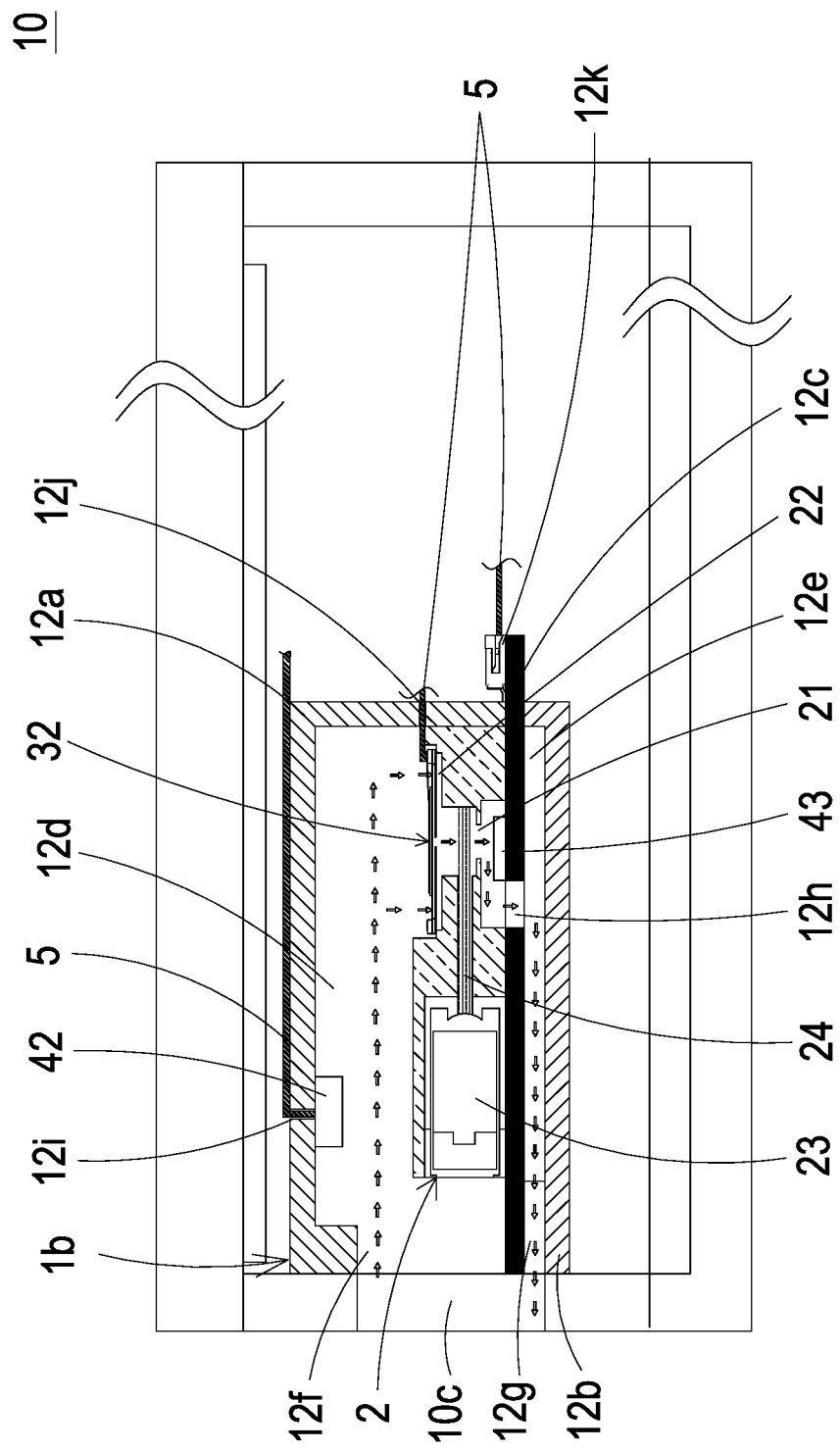
FIG. 5 is a schematic cross-sectional view illustrating the second separating chamber of the actuating and sensing module applied in the thin portable device of FIG. 3.
Figure 6A:
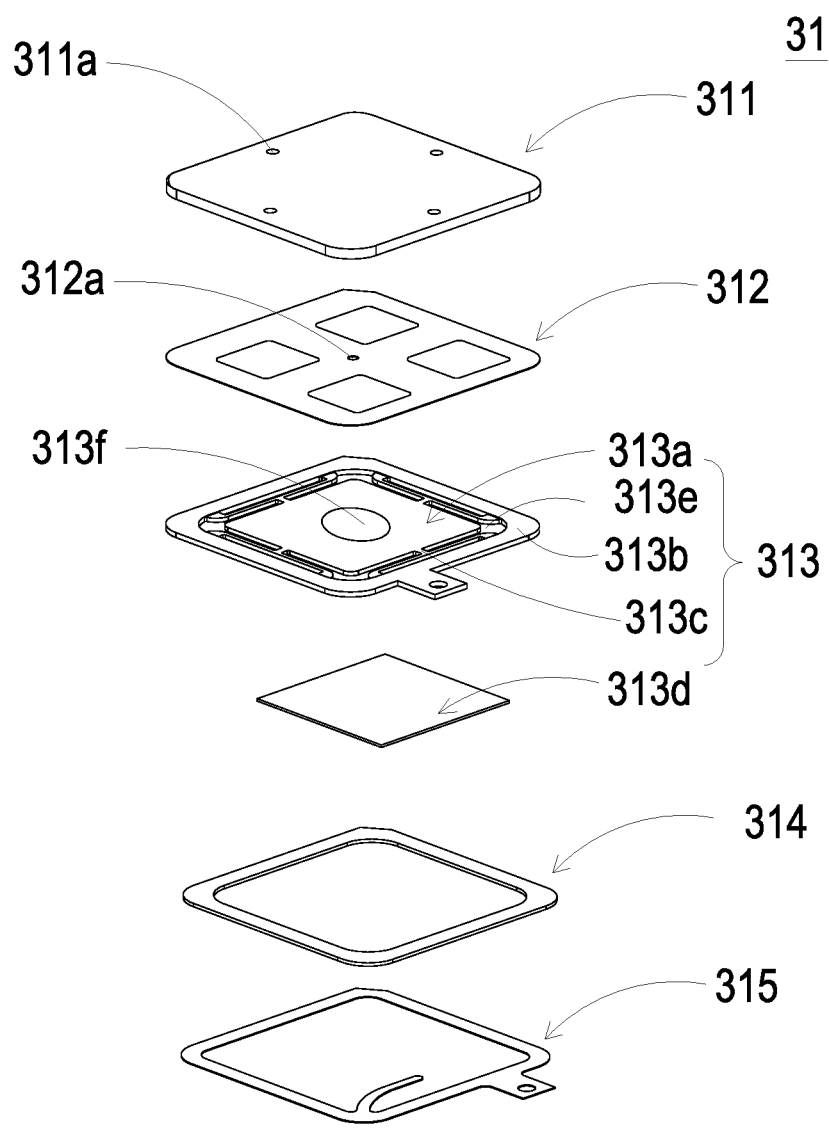
FIG. 6A is a schematic exploded view illustrating the first actuator of the actuating and sensing module of the present disclosure.
Figure 6B:
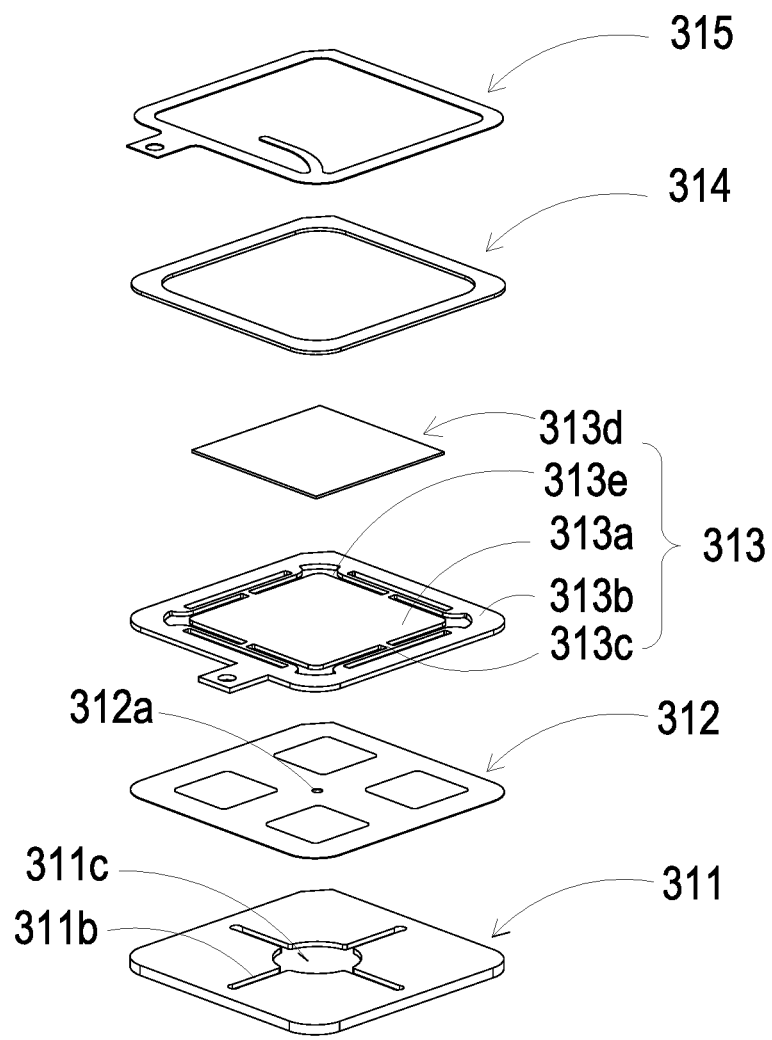
FIG. 6B is a schematic exploded view illustrating the first actuator of the actuating and sensing module of the present disclosure and taken along another viewpoint.

Please refer to FIGS. 3 to 5. The actuating and sensing module can be applied and assembled in a thin portable device 10. The thin portable device 10 includes a first opening 10a, a second opening 10b and a third opening 10c. The first opening 10a, the second opening 10b and the third opening 10c are opened on the same sidewall of the thin portable device 10. The actuating and sensing module is assembled within the thin portable device 10. The first inlet 11f and the first outlet 11g of the first separating chamber 1a are corresponding in position to the first opening 10a and the second opening 10b respectively. The second inlet 12f and the second outlet 12g of the second separating chamber 1b are corresponding in position to the third opening 10c. Thus, the gas outside the thin portable device 10 can be guided into the thin portable device 10 for monitoring. The first actuator 31 is actuated to guide the gas outside the thin portable device 10 into the second compartment 11e through the first compartment 11d, so that the negative pressure is formed in the first compartment 11d. The negative pressure allows the gas to be inhaled through the first inlet 11f to the first compartment 11d, and the gas flows to the second compartment 11e through the first communicating hole 11h. As the first actuator 31 is continuously actuated to transport the gas, the gas within the second compartment 11e is pushed and discharged from the first outlet 11g. Consequently, the one-way gas transportation and the gas monitoring are realized. On the other hand, the second actuator 32 guides the gas into the second separating chamber 1b. The second sensor 42 is configured to sense the temperature and moisture, and the third sensor 43 is configured to sense the concentration of the suspension particles. In an embodiment, the second sensor 42 is at least one selected from the group consisting of a temperature sensor and a moisture sensor. The actuating and sensing module of the present disclosure isolates the interfering factors (the interfering substances such as the heat generated by the internal actuators and the heat and gas pollution generated within the thin portable device 10) from affecting the plurality of sensors. Besides, the plurality of actuators, which are disposed for introducing and discharging the gas, enhance the rate of transporting the gas to the surface of the plurality of sensors for monitoring. The sensing efficiency of the plurality of sensors is increased. The present disclosure achieves the purpose of monitoring the gas with the actuating and sensing module that can reflect the actual condition in the environment. The characteristic of the gas to be monitored in the actuating and sensing module is the same as the characteristic of the gas outside the thin portable device 10.

After the descriptions about the characteristic of the actuating and sensing module, the structure and actions of the first actuator 31 and the second actuator 32 are described as follows.

Please refer to FIGS. 6A to 7A. In an embodiment, the first actuator 31 is a gas pump. The first actuator includes a gas inlet plate 311, a resonance plate 312, a piezoelectric actuator 313, an insulation plate 314 and a conducting plate 315, which are stacked on each other sequentially. The gas inlet plate 311 has at least one inlet aperture 311a, at least one convergence channel 311b and a convergence chamber 311c. The number of the inlet aperture 311a is the same as the number of the convergence channel 311b. In this embodiment, the number of the inlet aperture 311a and the convergence channel 311b is exemplified by four for each but not limited thereto. The four inlet apertures 311a penetrate through the four convergence channels 311b respectively, and the four convergence channels 311b converge to the convergence chamber 311c.

The resonance plate 312 is assembled on the gas inlet plate 311 by attaching. The resonance plate 312 has a central aperture 312a, a movable part 312b and a fixed part 312c. The central aperture 312a is located in the center of the resonance plate 312 and is aligned with the convergence chamber 311c of the gas inlet plate 311. The region of the resonance plate 312 around the central aperture 312a and corresponding to the convergence chamber 311c is the movable part 312b. The region of the periphery of the resonance plate 312 securely attached on the gas inlet plate 311 is the fixed part 312c.

The piezoelectric actuator 313 includes a suspension plate 313a, an outer frame 313b, at least one connecting part 313c, a piezoelectric element 313d, at least one vacant space 313e and a bulge 313f. The suspension plate 313a is a square suspension plate having a first surface 3131a and a second surface 3132a opposite to the first surface 3131a. The outer frame 313b is disposed around the periphery of the suspension plate 313a. The outer frame 313b has an assembling surface 3131b and a bottom surface 3132b opposite to the assembling surface 3131b. The at least one connecting part 313c is connected between the suspension plate 313a and the outer frame 313b for elastically supporting the suspension plate 313a. The at least one vacant space 313e is formed among the suspension plate 313a, the outer frame 313b and the at least one connecting part 313c for allowing the gas to flow through.

In addition, the first surface 3131a of the suspension plate 313a has the bulge 313f. In this embodiment, the formation of the bulge 313f may be completed by using an etching process, in which the region between the periphery of the bulge 313f and the junction at the least one connecting part 313c is partially removed. Accordingly, the bulge 313f of the suspension plate 313a is higher than the first surface 3131a, and a stepped structure is formed.

Figure 7A:
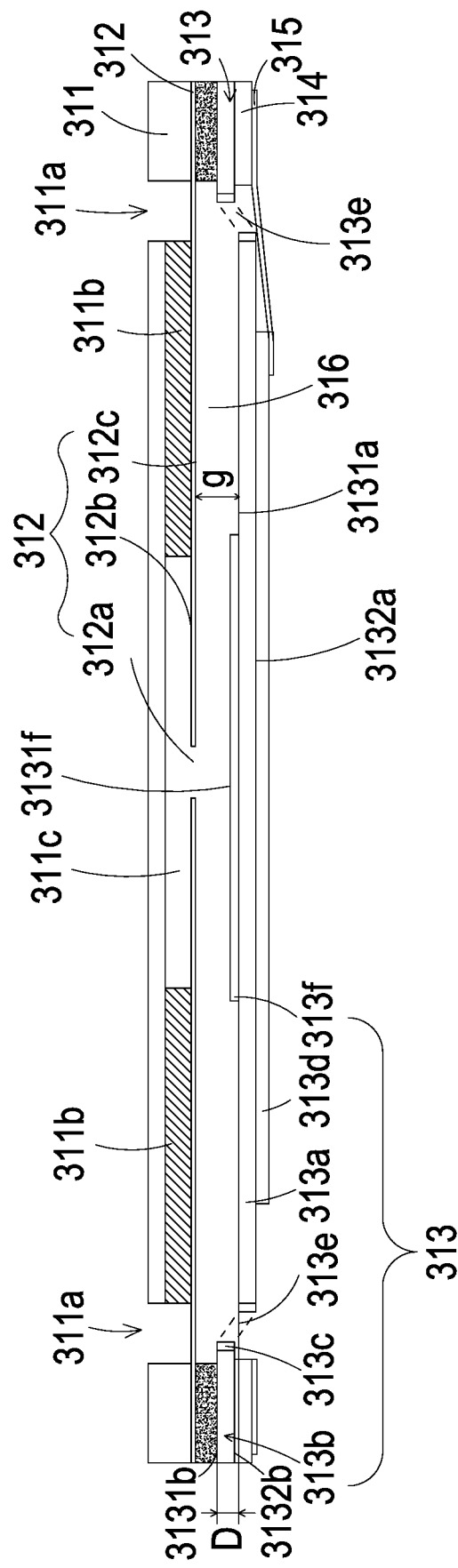
FIG. 7A is a schematic cross-sectional view illustrating the first actuator of the actuating and sensing module of the present disclosure.

As shown in FIG. 7A, in this embodiment, the suspension plate 313a may be further processed by using a stamping method, by which the outer frame 313b, the connecting part 313c, and the suspension plate 313a have a concave profile in cross section, as shown in FIG. 8A. The stamping method makes the suspension plate 313a disposed further away from the resonance plate 312 a distance D, which can be adjusted through the at least one connecting part 313c formed between the suspension plate 313a and the outer frame 313b. Consequently, the top surface 3131f of the bulge 313f and the first surface 3131a of the suspension plate 313a are not coplanar with the assembling surface 3131b of the outer frame 313b. Namely, the top surface 3131f of the bulge 313f and the first surface 3131a of the suspension plate 313a are lower than the assembling surface 3131b of the outer frame 313b, and the second surface 3132a of the suspension plate 313a is lower than the bottom surface 3132b of the outer frame 313b. In the embodiment, the piezoelectric element 313d is attached on the second surface 3132a of the suspension plate 313a and is disposed opposite to the bulge 313f. In response to an applied driving voltage, the piezoelectric element 313d is subjected to a deformation owing to the piezoelectric effect so as to drive the suspension plate 313a to bend and vibrate. In an embodiment, a small amount of adhesive is applied to the assembling surface 3131b of the outer frame 313b, and the piezoelectric actuator 313 is attached on the fixed part 312c of the resonance plate 312 after a hot pressing process. Therefore, the piezoelectric actuator 313 and the resonance plate 312 are assembled together.

In addition, the insulation plate 314 and the conducting plate 315 are both thin frame-shaped plate, which are stacked sequentially under the piezoelectric actuator 313. In this embodiment, the insulation plate 314 is attached on the bottom surface 3132b of the outer frame 313b of the piezoelectric actuator 313.

Please refer to FIG. 7A. The gas inlet plate 311, the resonance plate 312, the piezoelectric actuator 313, the insulation plate 314 and the conducting plate 315 of the first actuator 31 are stacked on each other sequentially. A chamber gap g is formed between the first surface 3131a of the suspension plate 313a and the resonance plate 312. Since the distance between the suspension plate 313a and the resonance plate 312 will influence the transportation effect of the first actuator 31, it is important to maintain the chamber gap g for providing a stable transportation efficiency of the first actuator 31. The suspension plate 313a of the first actuator 31 is processed by the stamping method as described above, and it makes the suspension plate 313a disposed further away from the resonance plate 312. Consequently, the first surface 3131a of the suspension plate 313a and the surface 3131f of the bulge 313f are not coplanar with the assembling surface 3131b of the outer frame 313b. Namely, the first surface 3131a of the suspension plate 313a and the surface 3131f of the bulge 313f are lower than the assembling surface 3131b of the outer frame 313b, and the second surface 3132a of the suspension plate 313a is lower than the bottom surface 3132b of the outer frame 313b. In this way, the entire structure may be improved by adopting the stamping method to process the suspension plate 313a. The space between the suspension plate 313a of the piezoelectric actuator 313 and the resonance plate 312 is adjustable due to the stamping method, by which the adjustable chamber gap g is realized. That is, the design of a chamber space 316 is improved by processing the suspension plate 313a of the piezoelectric actuator 313 to be disposed further away from the resonance plate 312. The desired chamber gap g can be satisfied by simply adjusting the distance D, as described above. It simplifies the structural design regarding the adjustment of the chamber gap g, and it also achieves the advantages of simplifying the process and shortening the processing time.

Figure 7B:
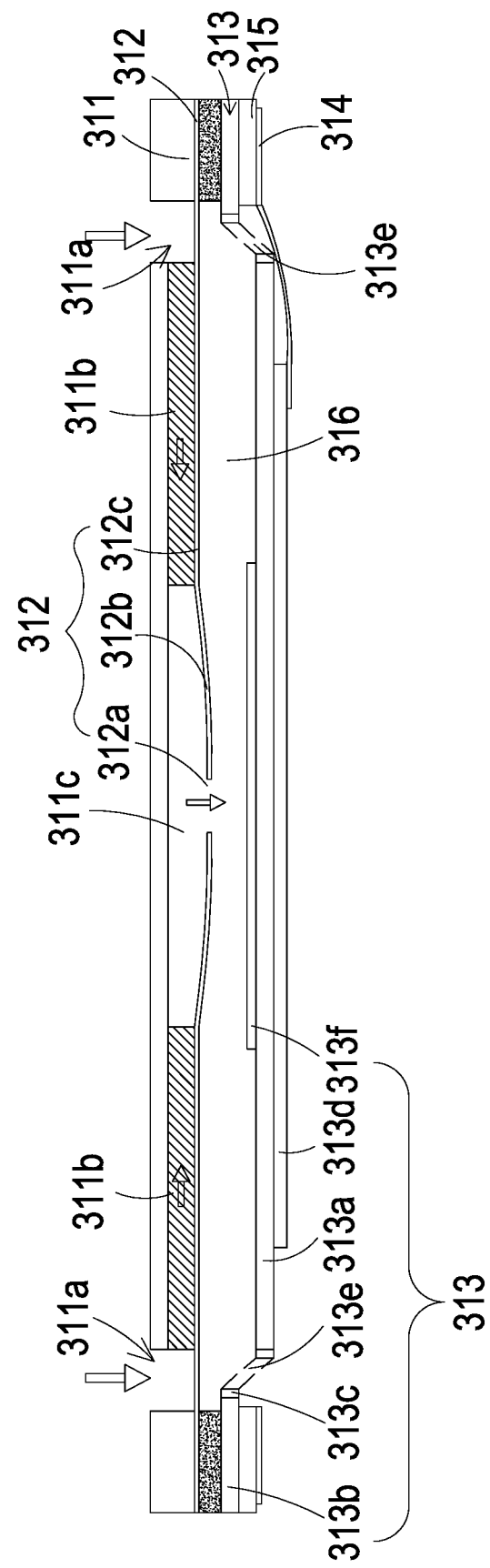
FIGS. 7B to 7D schematically illustrate the actions of the first actuator of the actuating and sensing module of the present disclosure.
Figure 7C:
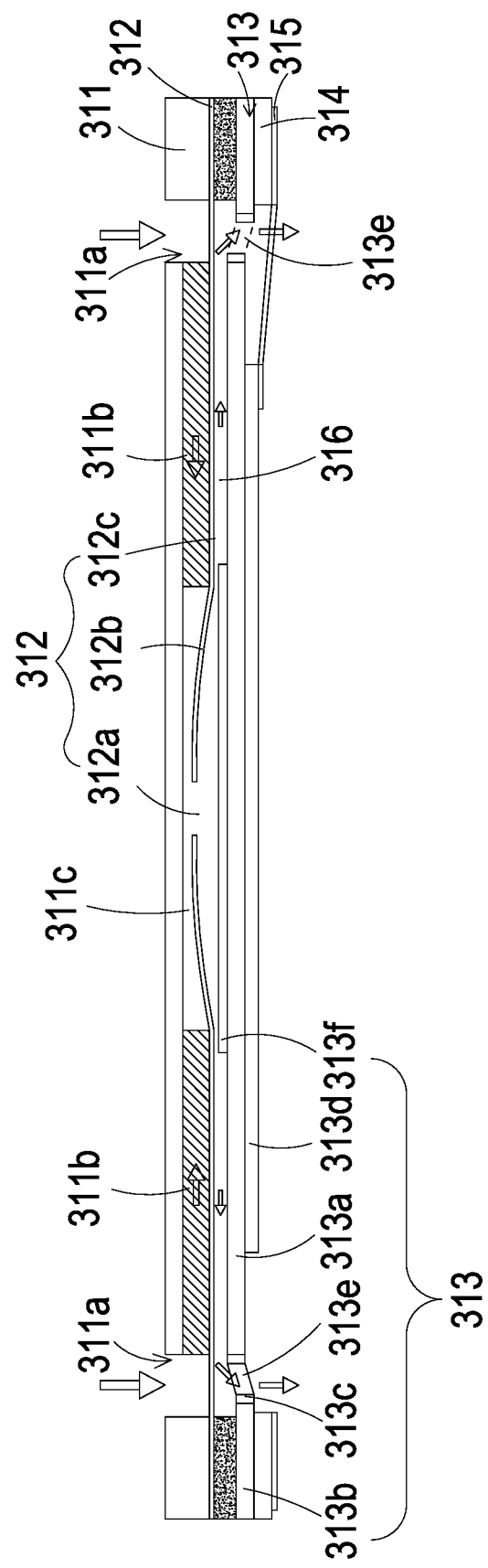
Figure 7D:
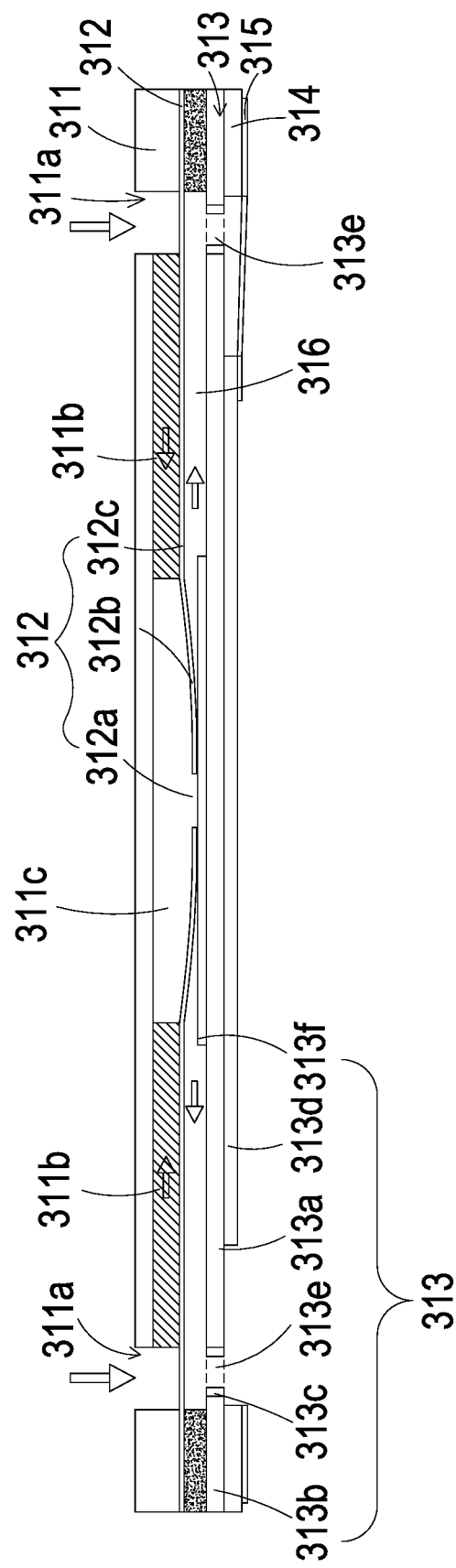

FIGS. 7B to 7D schematically illustrate the actions of the first actuator 31 of FIG. 7A. Please refer to FIG. 7B. When a driving voltage is applied to the piezoelectric element 313d of the piezoelectric actuator 313, the piezoelectric element 313d deforms to drive the suspension plate 313a to move in the direction away from the gas inlet plate 311. Meanwhile, the volume of the chamber space 316 is increased, and a negative pressure is formed in the chamber space 316 so that the air in the convergence chamber 311c is inhaled into the chamber space 316. At the same time, the resonance plate 312 is in resonance with the piezoelectric actuator 313 to move in the direction away from the gas inlet plate 311, so that the volume of the convergence chamber 311c is expanded. Since the air in the convergence chamber 311c is transported to the chamber space 316, a negative pressure is formed in the convergence chamber 311c. The negative pressure allows the air to be inhaled through the convergence channel 311b and the inlet aperture 311a to the convergence chamber 311c. Please refer to FIG. 7C. The piezoelectric element 313d drives the suspension plate 313a to move toward the gas inlet plate 311, and the volume of the chamber space 316 is compressed, so that the air in the chamber space 316 is forced to flow through the vacant space 313e in the direction away from the gas inlet plate 311. Thereby, the air transportation efficacy is achieved. Meanwhile, the resonance plate 312 is moved toward the gas inlet plate 311 in resonance with the suspension plate 313a, and the air in the convergence chamber 311c is pushed to move toward the chamber space 316 synchronously. Please refer to FIG. 7D. When the suspension plate 313a is driven to move in the direction away from the gas inlet plate 311, the resonance plate 312 is moved in the direction away from the gas inlet plate 311 in resonance with the suspension plate 313a. Meanwhile, the air in the chamber space 316 is compressed by the resonance plate 312 and is transferred toward the vacant space 313e. The volume of the convergence chamber 311c is expanded, and the air is allowed to flow through the inlet aperture 311a and the convergence channel 311b and converge in the convergence chamber 311c continuously. By repeating the above steps, the air is continuously introduced through the inlet aperture 311a into the first actuator 31, and then the air is transferred through the vacant space 313e in the direction away from the gas inlet plate 311. Consequently, the efficacy of transferring the air to the first sensor 41 is achieved. The air is continuously provided to the first sensor 41 for detection, thus the efficiency of detecting is increased.

Please refer to FIG. 7A. In another embodiment, by utilizing the micro-electro-mechanical technology, the first actuator 31 is a micro-electro-mechanical-system (MEMS) gas pump. Preferably but not exclusively, the gas inlet plate 311, the resonance plate 312, the piezoelectric actuator 313, the insulation plate 314 and the conducting plate 315 are manufactured by surface micromachining to reduce the volume of the first actuator 31.

Figure 8:
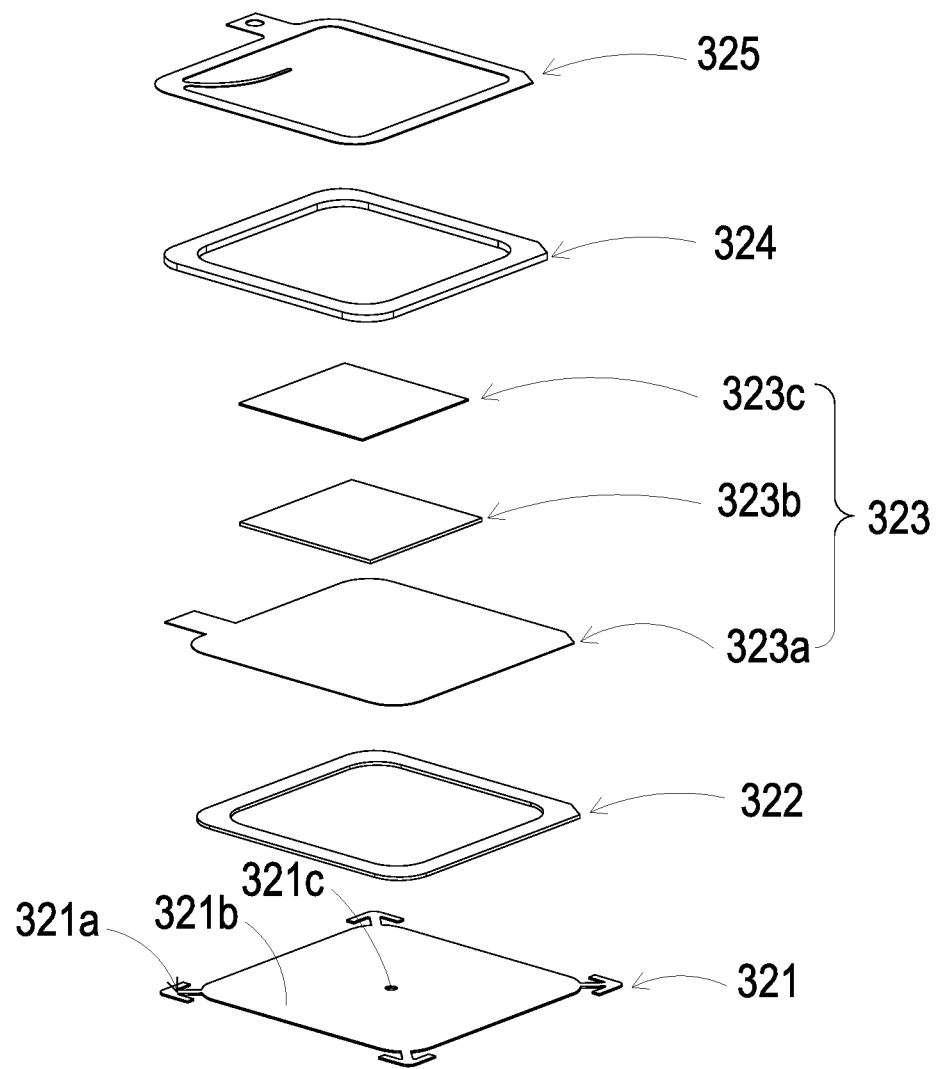
FIG. 8 is a schematic exploded view illustrating the second actuator of the actuating and sensing module of the present disclosure.

Please refer to FIG. 8. The second actuator 32 includes a nozzle plate 321, a chamber frame 322, an actuating element 323, an insulation frame 324 and a conducting frame 325, which are stacked on each other sequentially. The nozzle plate 321 includes a plurality of brackets 321a, a suspension board 321b and a central aperture 321c. The suspension board 321b is permitted to bend and vibrate. The plurality of brackets 321a are connected to the edge of the suspension board 321b. In this embodiment, there are four the brackets 321a, which are connected to four corners of the suspension board 321b respectively, but not limited thereto. The central aperture 321c is formed in the center of the suspension board 321b. The chamber frame 322 is carried and stacked on the suspension board 321b. The actuating element 323 is carried and stacked on the chamber frame 322, and includes a piezoelectric carrying plate 323a, an adjusting resonance plate 323b and a piezoelectric plate 323c. The piezoelectric carrying plate 323a is carried and stacked on the chamber frame 322. The adjusting resonance plate 323b is carried and stacked on the piezoelectric carrying plate 323a. The piezoelectric plate 323c is carried and stacked on the adjusting resonance plate 323b. As the piezoelectric plate 323c is actuated by an applied voltage, the piezoelectric plate 323c deforms to drive the piezoelectric carrying plate 323a and the adjusting resonance plate 323b to bend and vibrate in a reciprocating manner. The insulation frame 324 is carried and stacked on the piezoelectric carrying plate 323a of the actuating element 323. The conducting frame 325 is carried and the stacked on the insulation frame 324. A resonance chamber 326 is formed among the actuating element 323, the chamber frame 322 and the suspension board 321b. The adjusting resonance plate 323b is thicker than the piezoelectric carrying plate 323a. The adjusting resonance plate 323b is located between the piezoelectric plate 323c and the piezoelectric carrying plate 323a as a buffer for adjusting the vibration frequency of the piezoelectric carrying plate 323a. The thickness of the adjusting resonance plate 323b is larger than the thickness of the piezoelectric carrying plate 323a. The vibration frequency of the second actuator 32 can be adjusted by utilizing the adjusting resonance plate with different thickness, and thus the vibration frequency of the second actuator 32 is controlled to match with the vibration frequency of the nozzle plate 321. Preferably but not exclusively, the vibration frequency of the second actuator 32 is between 10 KHz and 30 kHz.

Figure 9A:
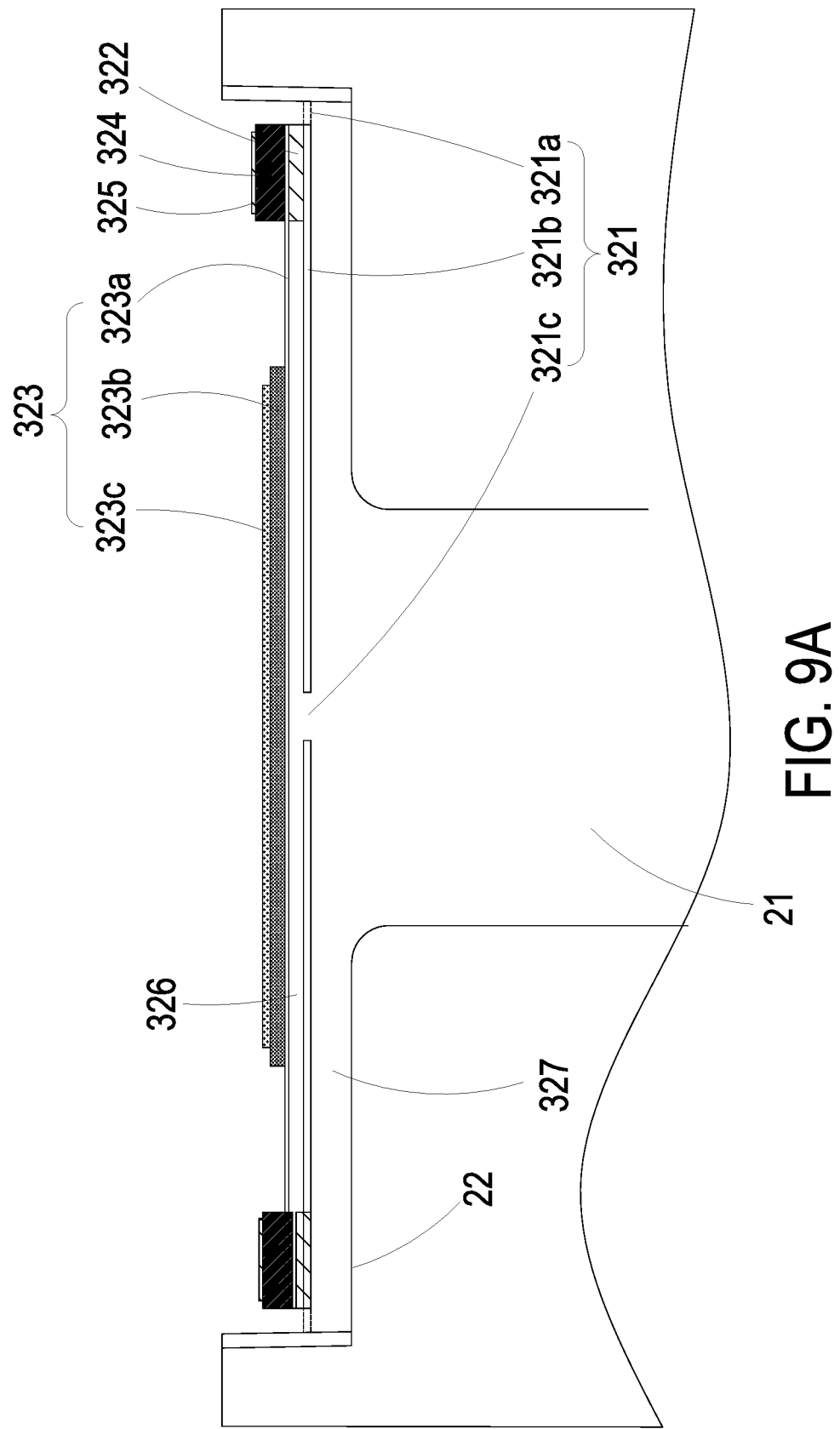
FIG. 9A is a schematic cross-sectional view illustrating the second actuator of the actuating and sensing module assembled on the particle monitoring base.
Figure 9B:
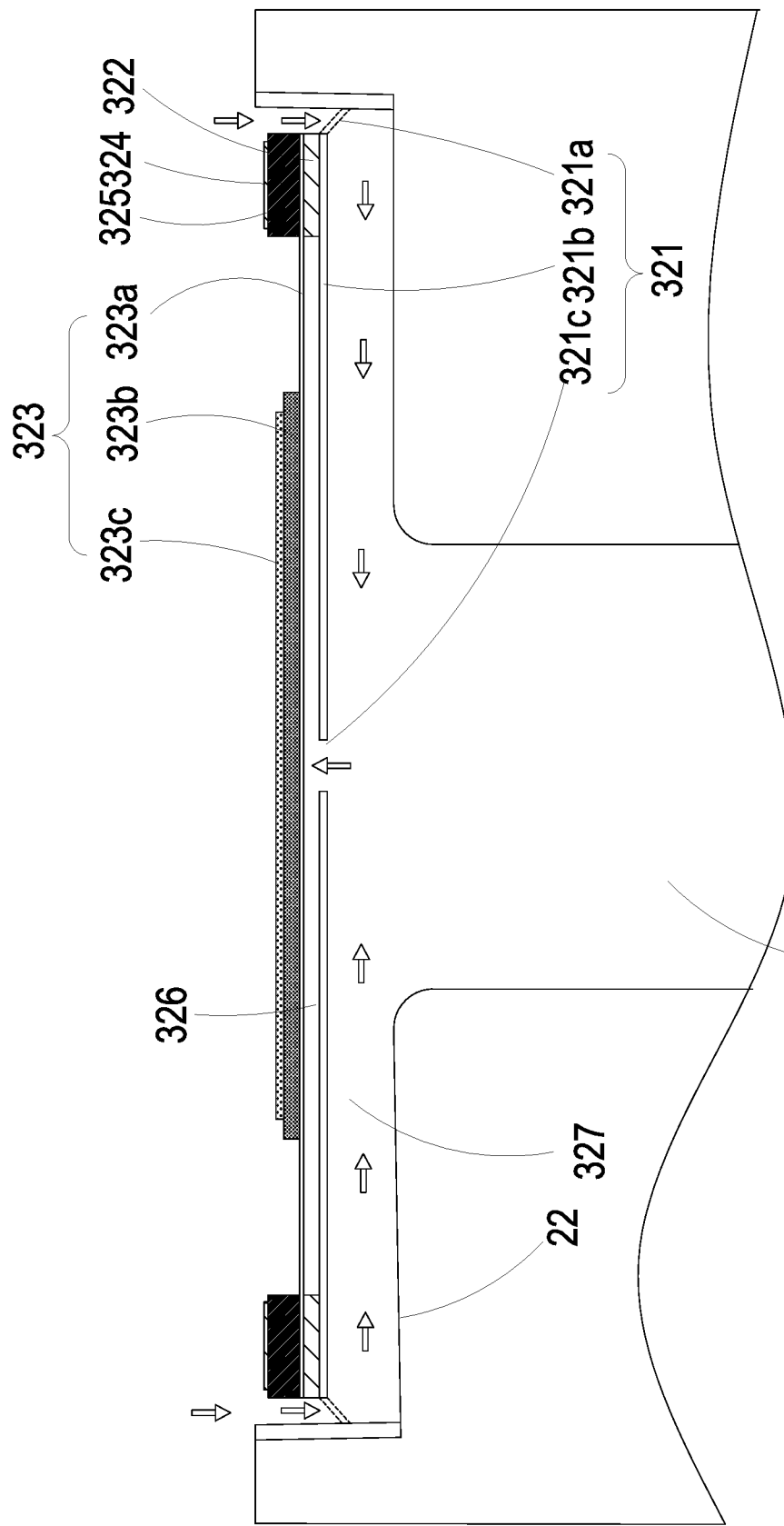

Please refer to FIGS. 9A to 9C. FIGS. 9B and 9C schematically illustrate the actions of the second actuator 32 of FIG. 9A. First, please refer to FIG. 9A. The second actuator 32 is disposed on the accommodation recess 22 of the particle monitoring base 2 via the plurality of brackets 321a. The nozzle plate 321 is disposed at a distance from the bottom of the accommodation recess 22, and an airflow chamber 327 is formed therebetween. Then, please refer to FIG. 9B. When the piezoelectric plate 323c of the actuating element 323 is actuated by an applied voltage, the piezoelectric plate 323c is subjected to a deformation owing to the piezoelectric elect, and the adjusting resonance plate 323b and the piezoelectric carrying plate 323a are driven to vibrate synchronously. Meanwhile, the nozzle plate 321 is driven to move owing to the Helmholtz resonance effect, and the actuating element 323 moves in a direction away from the bottom of the accommodation recess 22. Since the actuating element 323 moves in a direction away from the bottom of the accommodation recess 22, the volume of the airflow chamber 327 between the nozzle plate 321 and the bottom of the accommodation recess 22 is increased and a negative pressure is formed in the airflow chamber 327. The air outside the second actuator 32 is inhaled into the airflow chamber 327 through the vacant spaces among the plurality of bracket 321a of the nozzle plate 321 and the lateral wall of the accommodation recess 22 due to the pressure gradient, and is further compressed. Finally, please refer to FIG. 9C. The gas flows into the airflow chamber 327 continuously, and a positive pressure is formed in the airflow chamber 327. Meanwhile, the actuating element 323 is driven to vibrate in a direction toward the bottom of the accommodation recess 22 in response to the voltage, the volume of the airflow chamber 327 is compressed, and the gas in the airflow chamber 327 is pushed to flow into the monitoring channel 21. Thereby, the third sensor 43 can measure the concentration of the suspension particles in the gas flowing through the monitoring channel 21.

Figure 10:
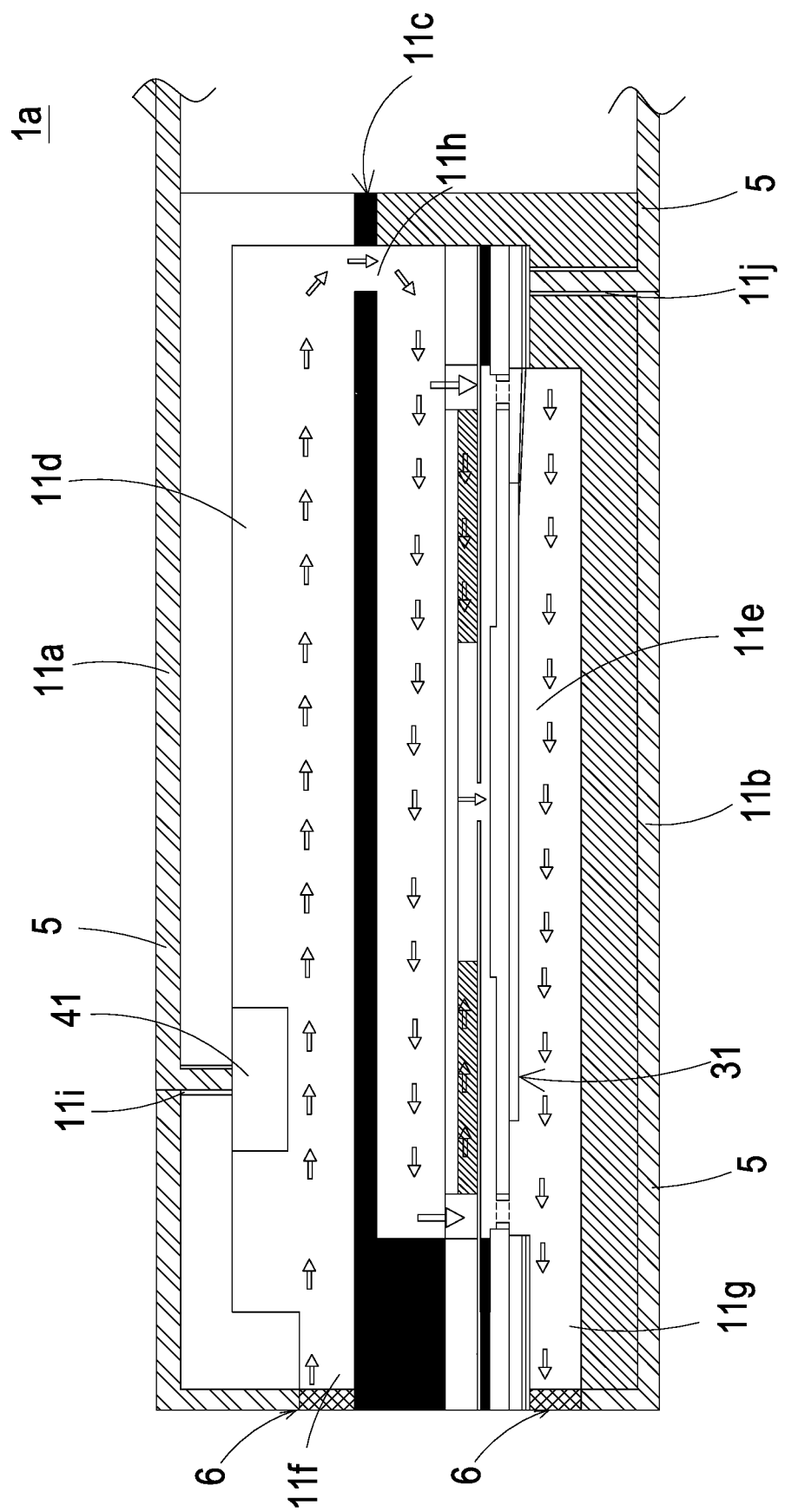
FIG. 10 is a schematic cross-sectional view illustrating a first separating chamber of an actuating and sensing module according to another embodiment of the present disclosure.

Please refer to FIG. 10. In some embodiments, the first separating chamber 1a of the actuating and sensing module further includes at least one valve 6. In this embodiment, the number of the valve 6 is two, and the two valves 6 are disposed at the first inlet 11f and the first outlet 11g respectively. The valves 6 seal the first inlet 11f and the first outlet 11g. The valves 6 are configured to open and close the first inlet 11f and the first outlet 11g. As the valves 6 are in the closed state, the interior space enclosed by the first separating chamber 1a is completely isolated from the environment outside the first separating chamber 1a, and vise versa. For example, in particular, since the boiling point of the volatile organic compound is relatively low and is easily affected by environmental factors, the valves 6 are utilized to close the first inlet 11f and the first outlet 11g during sensing the volatile organic compound. By the first body 11a and the second body 11b, the external factors are prevented from affecting the interior of the first separating chamber 1a. Moreover, the first actuator 31 is spatially separated from the first sensor 41 by the first partition 11c, and it prevents the first actuator 31 from interfering with the first sensor 41. Thus, the first sensor 41 can sense the quantity of the volatile organic compound actually contained in the air in the first separating chamber 1a without being affected by environmental factors.

Figure 11A:
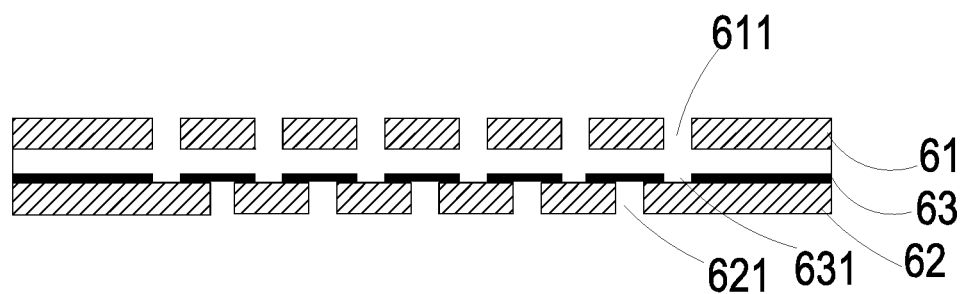
FIG. 11A is a schematic view illustrating a valve of the actuating and sensing module according to another embodiment of the present disclosure.
Figure 11B:
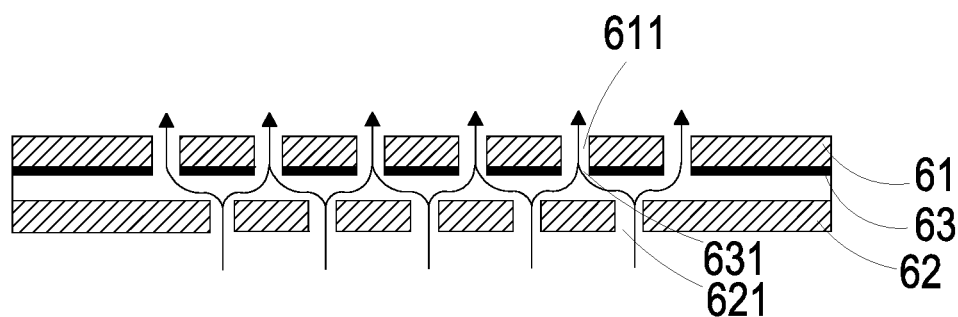
FIG. 11B schematically illustrate the actions of the valve of the actuating and sensing module according to another embodiment of the present disclosure.

Please refer to FIG. 11A and FIG. 11B. The valve 6 includes a stationary component 61, a sealing component 62 and a displacement component 63. The displacement component 63 is disposed and displaced between the stationary component 61 and the sealing component 62. The stationary component 61 has a plurality of first orifices 611. The displacement component 63 has a plurality of second orifices 631 corresponding in position to the plurality of first orifices 611 of the stationary component 61 respectively. That is, the plurality of first orifices 611 of the stationary component 61 are aligned with the plurality of second orifices 631 of the displacement component 63. The sealing component 62 has a plurality of third orifices 621. The plurality of third orifices 621 of the sealing component 62 are misaligned with the plurality of first orifices 611 of the stationary component 61. The stationary component 61, the sealing component 62 and the displacement component 63 of the valve 6 are controlled via a processor (not shown) connected to the flexible circuit board 5 so as to control the displacement component 63 to move toward the stationary component 61 and make the valve 6 in an open state.

In a first aspect of the valve 6 in the present disclosure, the displacement component 63 is made of a charged material, and the stationary component 61 is made of a bipolar conductive material. The stationary component 61 is controlled by the processor electrically connected to the flexible circuit board 5 so as to control the polarity (positive electrical polarity or the negative electrical polarity) of the stationary component 61. In the case that the displacement component 63 is made of a negatively charged material, and the valve 6 needs to be controlled to open, the stationary component 61 is controlled to form a positive electrode. In that, the displacement component 63 and the stationary component 61 are maintained in the opposite polarity, so that the displacement component 63 moves toward and attaches to the stationary component 61, and the valve 6 is in an open state (as shown in FIG. 11B). Alternatively, in case that the displacement component 63 is made of a negative-charged material, and the valve 6 needs to be controlled to close, the stationary component 61 is controlled to form a negative electrode. In that, the displacement component 63 and the stationary component 61 are maintained in the same polarity, so that the displacement component 63 moves toward and attaches to the sealing component 62, and the valve 6 is in a closed state (as shown in FIG. 11A).

In a second aspect of the valve 6 in the present disclosure, the displacement component 63 is made of a magnetic material, and the stationary component 61 is made of an electromagnet material and can be controlled to change its magnetic polarity. The stationary component 61 is controlled by the processor electrically connected to the flexible circuit board 5, so as to control the polarity (positive magnetic polarity or negative magnetic polarity) of the stationary component 61. In case that the displacement component 63 is made of a negative-magnetic material, and the valve 6 needs to be controlled to open, the stationary component 61 is controlled to form a positive-magnetic pole. In that, the displacement component 63 and the stationary component 61 are maintained in the opposite polarity, so that the displacement component 63 moves toward and attaches to the stationary component 61, and the valve 6 is in the open state (as shown in FIG. 11B). Alternatively, in case that the displacement component 63 is made of a negative-magnetic material, and the valve 6 needs to be controlled to close, the stationary component 61 is controlled to form a negative-magnetic pole. In that, the displacement component 63 and the stationary component 61 are maintained in the same polarity, so that the displacement component 63 moves toward and attaches to the sealing component 62, and the valve 6 is in the closed state (as shown in FIG. 11A).

Figure 12:
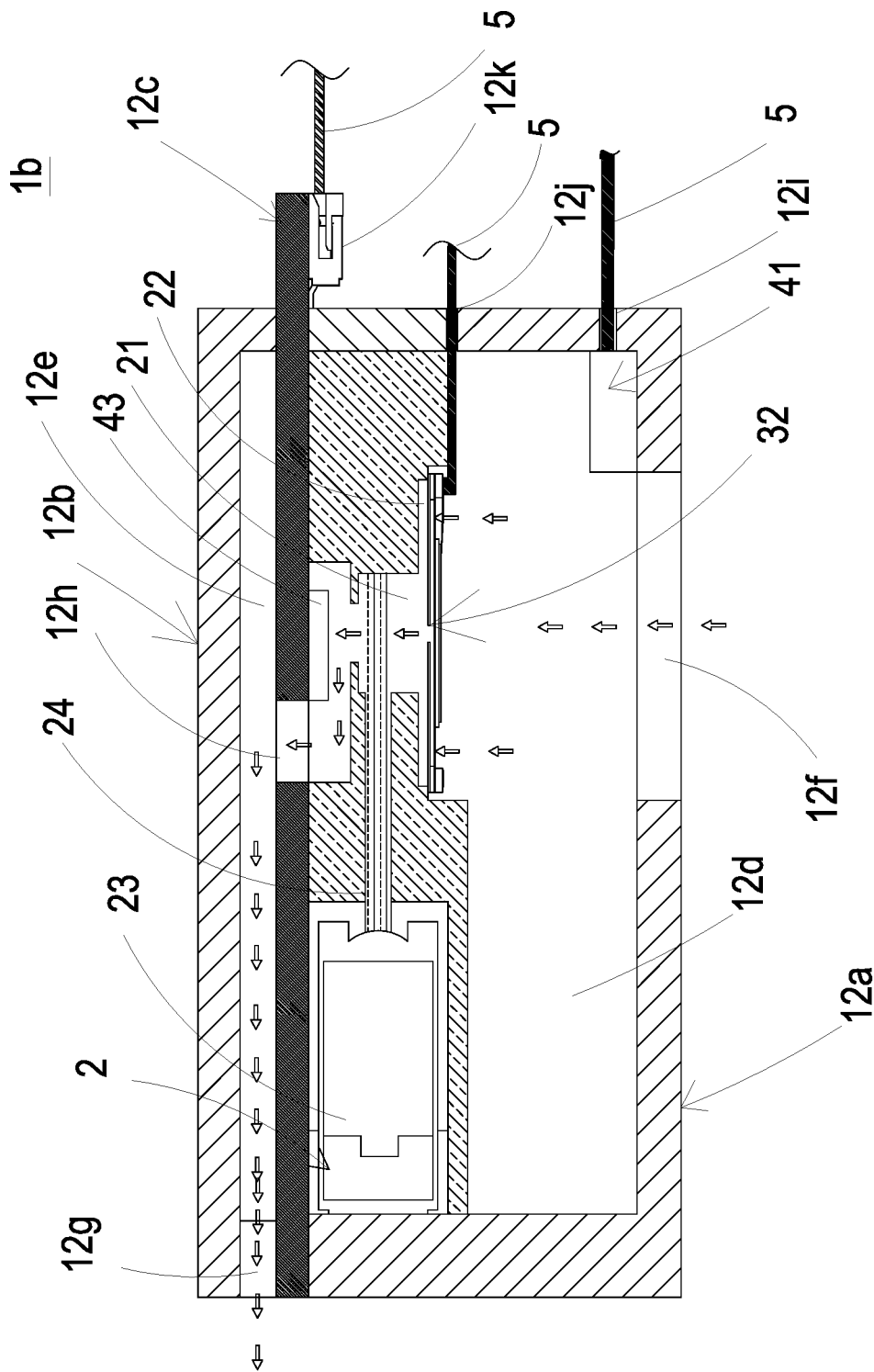
FIG. 12 is a schematic cross-sectional view illustrating a third separating chamber of the actuating and sensing module according to another embodiment of the present disclosure.

Please refer to FIG. 12. In another embodiment of the second separating chamber 1b of the actuating and sensing module of the present disclosure, the second inlet 12f is aligned with the monitoring channel 21. That is, the second inlet 12f is disposed directly under the monitoring channel 21. Before reaching the monitoring channel 21, the gas may flow along a gas flow path (indicated by the arrows) perpendicular to the monitoring channel 21, as shown in FIG. 2. However, in the embodiment illustrated in FIG. 12, it efficiently reduces the gas flow path perpendicular to the monitoring channel 21, or, more accurately speaking, the position of the second inlet 12f disposed directly under the monitoring channel 21 makes the gas flow path connect to the monitoring channel 21 in a straight direction. The flowing resistance of the flowing path is reduced as low as possible. When the second actuator 32 is actuated, the air introduced from the second inlet 12f directly flows along the straight direction into the monitoring channel 21 without hindrance, so as to enhance the efficiency of gas transportation.

Figure 13:
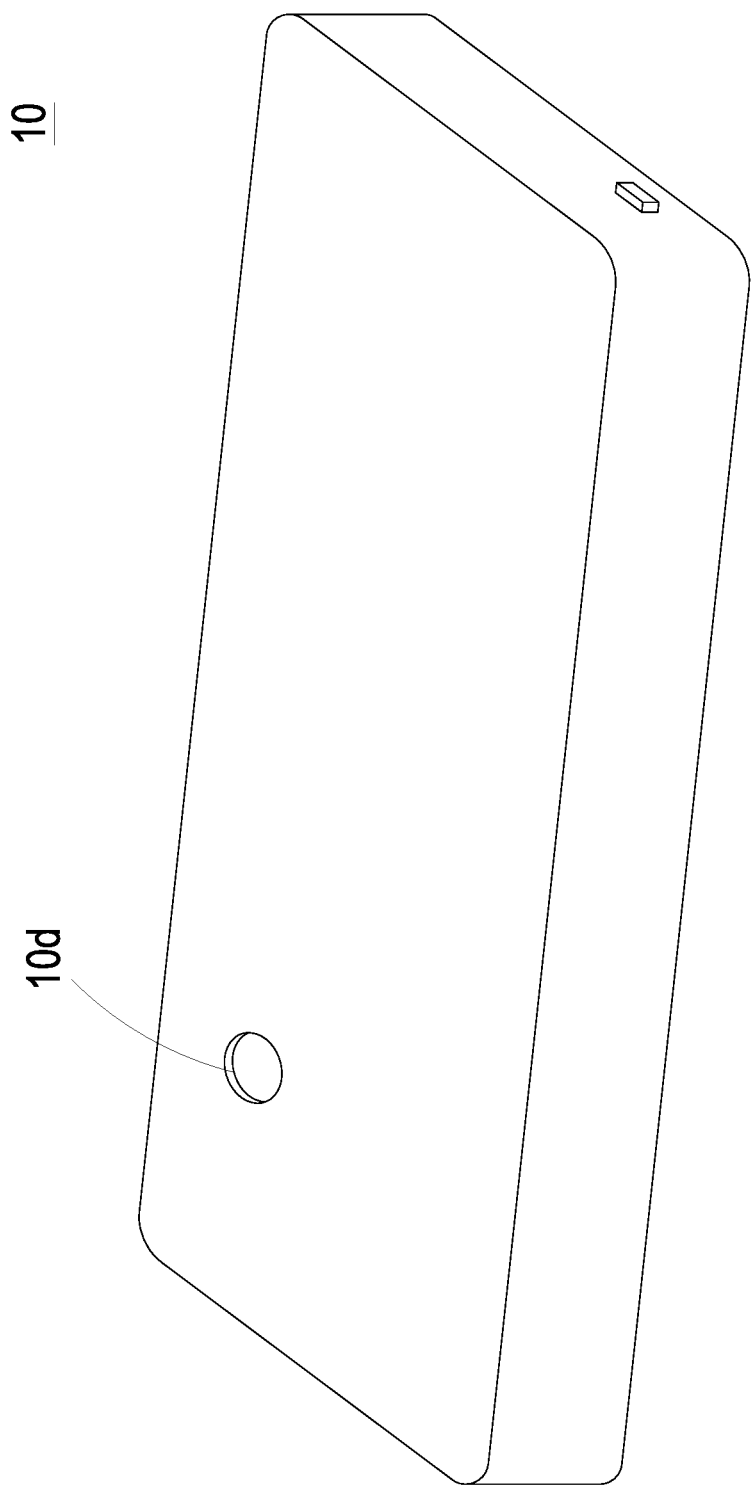
FIG. 13 is schematic view showing a fourth opening, wherein the third separating chamber of the actuating and sensing module is applied in the thin portable device.
Figure 14:
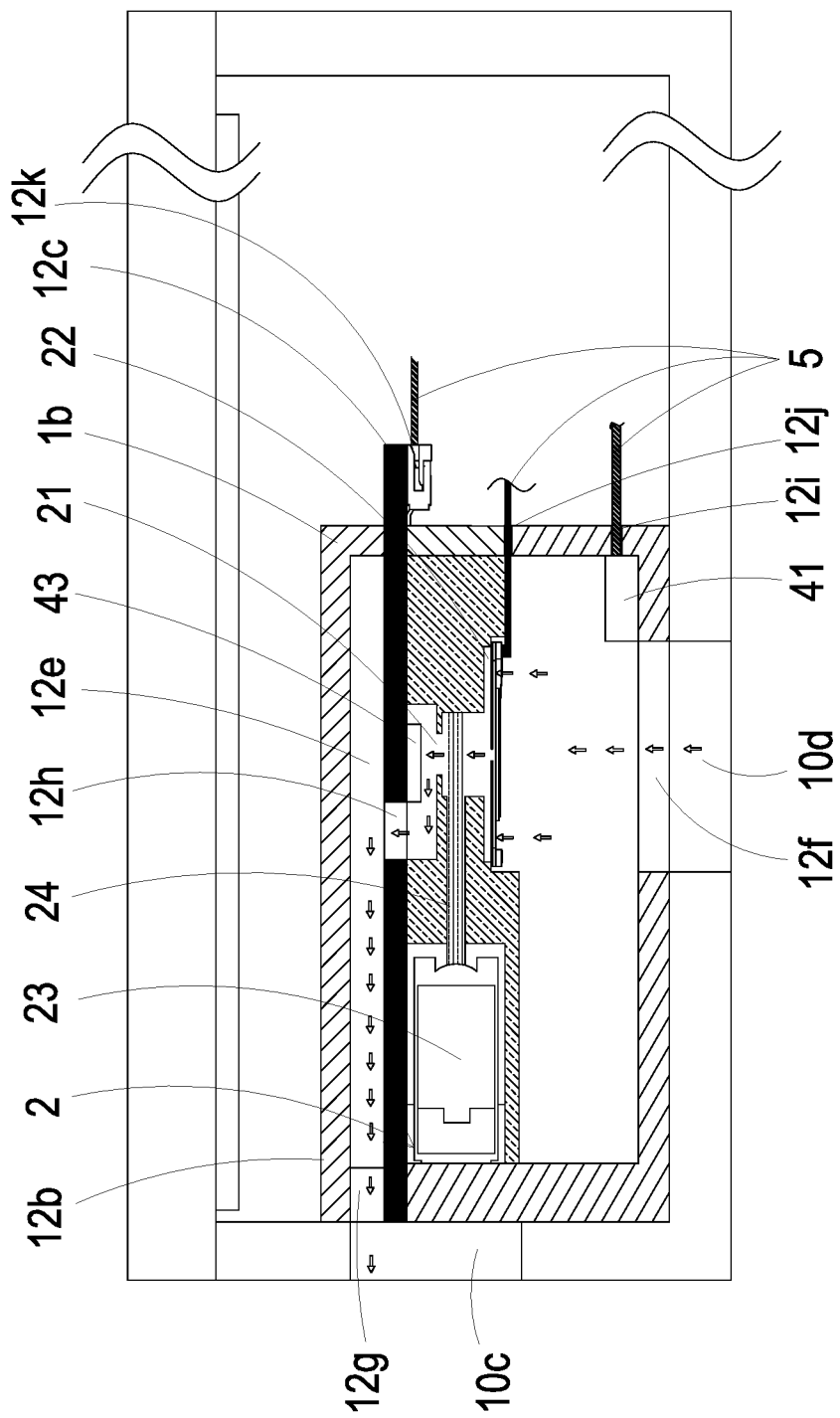
FIG. 14 is a schematic cross-sectional view illustrating the third separating chamber of the actuating and sensing module applied in the thin portable device.

Please refer to FIG. 13 and FIG. 14. In this embodiment of the second separating chamber 1b, the actuating and sensing module is assembled in the thin portable device 10. The thin portable device 10 further includes a fourth opening 10d. The third opening 10c of the thin portable device 10 is directly corresponding in position to the second outlet 12g of the second separating chamber 1b. The fourth opening 10d is directly corresponding in position to the second inlet 12f of the second separating chamber 1b. Consequently, the gas is guided into and discharged from the second separating chamber 1b in direct gas convection, and the efficacy of gas transportation is enhanced.

From the above descriptions, the present disclosure provides an actuating and sensing module. With the design of the concave profile, the actuator is capable of introducing the gas into the actuating and sensing module rapidly and stably. Thus, the efficiency of sensing is enhanced. By disposing a plurality of separating chambers, the plurality of sensors are separated from each other. When the plurality of sensors sense at the same time, the sensors are free from interference from each other and other actuators. If the gas outside the thin portable device is guided thereinto by the actuating and sensing module for monitoring, the monitoring result is not affected by the processor or other elements inside the thin portable device. Consequently, the actuating and sensing module is capable of guiding the gas into the thin portable device for monitoring anytime and anywhere.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. An actuating and sensing module, comprising:
   a main body comprising a plurality of separating chambers, the plurality of separating chambers comprising:
   a first separating chamber having a first partition, a first inlet and a first outlet, wherein interior space inside the first separating chamber is divided into a first compartment and a second compartment by the first partition, the first inlet is in fluid communication with the first compartment, and the first outlet is in fluid communication with the second compartment, wherein the first partition has a first communicating hole, and the first compartment and the second compartment are in fluid communication with each other through the first communicating hole; and a second separating chamber assembled with the first separating chamber as a whole, and having a supporting partition, a second inlet, and a second outlet, wherein interior space inside the second separating chamber is divided into a third compartment and a fourth compartment by the supporting partition, the second inlet is in fluid communication with the third compartment, and the second outlet is in fluid communication with the fourth compartment, wherein the supporting partition has a second communicating hole, and the third compartment and the fourth compartment are in fluid communication with each other through the second communicating hole;

a particle monitoring base disposed between the third compartment and the supporting partition of the second separating chamber, wherein the particle monitoring base has a monitoring channel and an accommodation recess, wherein the accommodation recess is disposed on an end of the monitoring channel and in fluid communication with the monitoring channel;

a plurality of actuators comprising:
  a first actuator disposed between the second compartment and the first partition, wherein gas is introduced into the first compartment through the first inlet, transported to the second compartment through the first communicating hole, and discharged through the first outlet by the first actuator, whereby an one-way gas transportation in the first separating chamber is formed; and
  a second actuator disposed within the accommodation recess of the particle monitoring base and sealing the end of the monitoring channel, the gas is introduced into the third compartment through the second inlet, guided into the monitoring channel, transported to the fourth compartment through the second communicating hole, and discharged through the second outlet by the second actuator, whereby an one-way gas transportation in the second separating chamber is formed; and a plurality of sensors comprising:
  a first sensor disposed in the first compartment and separated from the first actuator, wherein the first sensor is configured to monitor the gas on a surface of the first sensor;
  a second sensor disposed in the third compartment and configured to monitor the gas guided into the third compartment; and
  a third sensor carried on the supporting partition and located in the monitoring channel of the particle monitoring base, wherein the third sensor is configured to monitor the gas guided into the monitoring channel.

2. The actuating and sensing module according to claim 1, wherein the first separating chamber comprises a first body and a second body assembled with each other, the first partition is disposed between the first body and the second body, the first compartment is formed between the first body and the first partition, the second compartment is formed between the second body and the first partition, the first inlet is disposed between the first body and the first partition and is in fluid communication with the first compartment, and the first outlet is disposed between the second body and the first partition and is in fluid communication with the second compartment.

3. The actuating and sensing module according to claim 1, wherein the second separating chamber comprises a third body and a fourth body assembled with each other, the supporting partition is disposed between the third body and the fourth body, the third compartment is formed between the third body and the supporting partition, the fourth compartment is formed between the fourth body and the supporting partition, the second inlet is disposed between the third body and the supporting partition and is in fluid communication with the third compartment, and the second outlet is disposed between the fourth body and the supporting partition and is in fluid communication with the fourth compartment.

4. The actuating and sensing module according to claim 1, wherein the first sensor is a gas sensor, the second sensor is at least one selected from the group consisting of a temperature sensor and a moisture sensor, the third sensor is a light sensor, and the light sensor is a PM 2.5 sensor.

5. The actuating and sensing module according to claim 4, wherein the gas sensor includes at least one selected from the group consisting of an oxygen sensor, a carbon monoxide sensor, a carbon dioxide sensor, a temperature sensor, an ozone sensor, a volatile organic compound sensor, a bacterium sensor, a virus sensor, a microorganism sensor and combinations thereof.

6. The actuating and sensing module according to claim 1, wherein the first actuator is a gas pump and comprises: a gas inlet plate having at least one inlet aperture, at least one convergence channel and a convergence chamber, wherein the at least one inlet aperture allows the air to flow in, the convergence channel is disposed corresponding to the inlet aperture and guides the air from the inlet aperture toward the convergence chamber; a resonance plate having a central aperture and a movable part, wherein the central aperture is aligned with the convergence chamber, and the movable part surrounds the central aperture; and a piezoelectric actuator aligned with the resonance plate and comprising: a suspension plate being a square suspension plate and having a first surface, a second surface and a bulge, wherein the bulge is formed on the first surface; an outer frame arranged around the suspension plate and having an assembling surface; at least one bracket connected between the suspension plate and the outer fra me for elastically supporting the suspension plate; and a piezoelectric element attached on the second surface of the suspension plate, wherein when a voltage is applied to the piezoelectric element, the suspension plate is driven to undergo a bending vibration, wherein the at least one bracket is formed between the suspension plate and the outer frame, the first surface of the suspension plate and the assembling surface of the outer frame are non-coplanar, and a chamber gap is maintained between the first surface of the suspension plate and the resonance plate, wherein a gap is formed between the resonance space and the piezoelectric actuator to define a chamber space, so that the air from the at least one inlet aperture of the gas inlet plate is converged to the convergence chamber along the at least one convergence channel and flows through the central a perture of the resonance plate when the piezoelectric actuator is enabled, whereby the air is further transferred through a resonance between the piezoelectric actuator and the mova ble part of the resonance plate.

7. The actuating and sensing module according to claim 2, wherein the first body has a first connecting perforation configured for a flexible circuit board to penetrate therethrough and connect to the first sensor, the first connecting perforation is sealed by a potting compound after connecting the flexible circuit board to the first sensor, the second body has a second connecting perforation configured for a flexible circuit board to penetrate therethrough and connect to the first actuator, and the second connecting perforation is sealed by a potting compound after connecting the flexible circuit board to the first actuator.

8. The actuating and sensing module according to claim 3, wherein the third body has a third connecting perforation configured for a flexible circuit board to penetrate therethrough and connect to the second sensor, the third connecting perforation is sealed by a potting compound after connecting the flexible circuit board to the second sensor, the third body has a fourth connecting perforation configured for a flexible circuit board to penetrate therethrough and connect to the second actuator, and the fourth connecting perforation is sealed by a potting compound after connecting the flexible circuit board to the second actuator.

9. The actuating and sensing module according to claim 1, wherein the second actuator comprises:
- a nozzle plate comprising a plurality of brackets, a suspension board and a central aperture, wherein the suspension board is permitted to bend and vibrate, the plurality of brackets are adjacent to and connected to edges of the suspension board, the central aperture is formed in and aligned with a center of the suspension board, the second actuator is disposed on the accommodation recess of the particle monitoring base through the plurality of brackets, the plurality of brackets elastically support the suspension board, an airflow chamber is formed between the nozzle plate and the accommodation recess, and at least one vacant space is formed among the plurality brackets and the suspension board;
- a chamber frame carried and stacked on the suspension board;
- an actuating element carried and stacked on the chamber frame, wherein the actuation element is configured to bend and vibrate in a reciprocating manner by an applied voltage, and the actuating element comprises:
  - a piezoelectric carrying plate carried and stacked on the chamber frame;
  - an adjusting resonance plate carried and stacked on the piezoelectric carrying plate, wherein a thickness of the adjusting resonance plate is larger than a thickness of the piezoelectric carrying plate; and
  - a piezoelectric plate carried and stacked on the adjusting resonance plate, wherein the piezoelectric plate is configured to drive the piezoelectric carrying plate and the adjusting resonance plate to bend and vibrate in the reciprocating manner by the applied voltage;
- an insulation frame carried and stacked on the actuating element; and
- a conducting frame carried and stacked on the insulation frame,
- wherein a resonance chamber is formed among the actuating element, the chamber frame and the suspension board collaboratively, wherein when the voltage is applied to the actuating element, the actuating element drives the nozzle plate to vibrate in resonance, the suspension board of the nozzle plate is driven to vibrate in the reciprocating manner, so as to make the gas flow through the at least one vacant space into the airflow chamber and discharged through the monitoring channel to achieve air transportation.

10. An actuating and sensing module, comprising:
- at least one main body comprising a plurality of separating chambers, the plurality of separating chambers comprising:
  - at least one first separating chamber having at least one first partition, at least one first inlet and at least one first outlet, wherein interior space inside the first separating chamber is divided into at least one first compartment and at least one second compartment by the first partition, the first inlet is in fluid communication with the first compartment, and the first outlet is in fluid communication with the second compartment, wherein the first partition has at least one first communicating hole, and the first compartment and the second compartment are in fluid communication with each other through the at least one first communicating hole; and
  - at least one second separating chamber assembled with the first separating chamber as a whole, and having at least one supporting partition, at least one second inlet, and at least one second outlet, wherein interior space inside the second separating chamber is divided into at least one third compartment and at least one fourth compartment by the supporting partition, the second inlet is in fluid communication with the third compartment, and the second outlet is in fluid communication with the fourth compartment, wherein the supporting partition has at least one second communicating hole, and the third compartment and the fourth compartment are in fluid communication with each other through the at least one second communicating hole;
- at least one particle monitoring base disposed between the third compartment and the supporting partition of the second separating chamber, wherein the particle monitoring base has at least one monitoring channel, and at least one accommodation recess, wherein the accommodation recess is disposed on an end of the monitoring channel and in fluid communication with the monitoring channel;
- a plurality of actuators comprising:
  - at least one first actuator disposed between the second compartment and the first partition, wherein gas is introduced into the first compartment through the first inlet, transported to the second compartment through the first communicating hole, and discharged through the first outlet by the first actuator, whereby an one-way gas transportation in the first separating chamber is formed; and
  - at least one second actuator disposed within the accommodation recess of the particle monitoring base and sealing the end of the monitoring channel, the gas is introduced into the third compartment through the second inlet, guided into the monitoring channel, transported to the fourth compartment through the second communicating hole, and discharged through the second outlet by the second actuator, whereby an one-way gas transportation in the second separating chamber is formed; and
- a plurality of sensors comprising:
  - at least one first sensor disposed in the first compartment and separated from the first actuator, wherein the first sensor is configured to monitor the gas on a surface of the first sensor;
  - at least one second sensor disposed in the third compartment and configured to monitor the gas guided into the third compartment; and
  - at least one third sensor carried on the supporting partition and located in the monitoring channel of the particle monitoring base, wherein the third sensor is configured to monitor the gas guided into the monitoring channel.

* * * * *